United States Patent
Shamshiev et al.

(10) Patent No.: US 11,434,294 B2
(45) Date of Patent: Sep. 6, 2022

(54) BINDING MEMBERS TO PD-L1

(71) Applicant: CELL MEDICA INC., Houston, TX (US)

(72) Inventors: Abdijapar Shamshiev, Zürich (CH); Titus Kretzschmar, Hünenberg (CH); Miriam Droste, Dietikon (CH); Douglas Phillips, Schlieren (CH)

(73) Assignee: Cell Medica, Inc., Houston, TX (US)

( * ) Notice: Subject to any disclaimer, the term of this patent is extended or adjusted under 35 U.S.C. 154(b) by 405 days.

(21) Appl. No.: 16/079,210

(22) PCT Filed: Feb. 24, 2017

(86) PCT No.: PCT/EP2017/054367
§ 371 (c)(1),
(2) Date: Aug. 23, 2018

(87) PCT Pub. No.: WO2017/144681
PCT Pub. Date: Aug. 31, 2017

(65) Prior Publication Data
US 2019/0055312 A1 Feb. 21, 2019

(30) Foreign Application Priority Data
Feb. 25, 2016 (EP) .................................. 16020057

(51) Int. Cl.
| C07K 16/28 | (2006.01) |
| A61K 39/395 | (2006.01) |
| A61K 35/17 | (2015.01) |
| A61K 39/39 | (2006.01) |
| A61P 35/00 | (2006.01) |
| A61K 39/00 | (2006.01) |
| A61K 45/06 | (2006.01) |
| C07K 14/705 | (2006.01) |
| G01N 33/68 | (2006.01) |

(52) U.S. Cl.
CPC .......... *C07K 16/2827* (2013.01); *A61K 35/17* (2013.01); *A61K 39/0011* (2013.01); *A61K 39/39* (2013.01); *A61K 39/39591* (2013.01); *A61K 45/06* (2013.01); *A61P 35/00* (2018.01); *C07K 14/705* (2013.01); *G01N 33/6872* (2013.01); *A61K 2039/505* (2013.01); *A61K 2039/5156* (2013.01); *A61K 2039/545* (2013.01); *C07K 2317/24* (2013.01); *C07K 2317/33* (2013.01); *C07K 2317/52* (2013.01); *C07K 2317/622* (2013.01); *C07K 2317/73* (2013.01); *C07K 2317/76* (2013.01); *C07K 2317/92* (2013.01); *C07K 2317/94* (2013.01); *C07K 2319/03* (2013.01); *G01N 2333/70532* (2013.01)

(58) Field of Classification Search
None
See application file for complete search history.

(56) References Cited

U.S. PATENT DOCUMENTS

| 5,506,121 A | 5/1996 | Skerra et al. |
| 6,103,493 A | 8/2000 | Skerra et al. |
| 8,217,149 B2 | 7/2012 | Irving et al. |
| 8,779,108 B2 | 7/2014 | Queva et al. |
| 2003/0083474 A1 | 5/2003 | Schmidt et al. |
| 2010/0203056 A1* | 8/2010 | Irving .................... A61K 39/00 424/139.1 |
| 2015/0203580 A1 | 7/2015 | Papadopoulos et al. |
| 2016/0009805 A1 | 1/2016 | Kowanetz et al. |

FOREIGN PATENT DOCUMENTS

| EP | 2079760 B1 | 12/2007 | |
| EP | 2158315 B1 | 6/2008 | |
| WO | 2009/155725 A1 | 12/2009 | |
| WO | 2009/155726 A2 | 12/2009 | |
| WO | 2010/077634 A1 | 7/2010 | |
| WO | WO 2010/077634 A1 | 7/2010 | |
| WO | 2011/066389 A1 | 6/2011 | |
| WO | WO 2011/066389 A1 | 6/2011 | |
| WO | 2013/079174 | 6/2013 | |
| WO | 2013/182912 A2 | 12/2013 | |
| WO | WO 2014/134165 | * 9/2014 | ............... C12N 5/10 |
| WO | 2014/206561 | 12/2014 | |
| WO | 2015/038538 A1 | 3/2015 | |
| WO | 2015/112805 A1 | 7/2015 | |
| WO | 2017/144681 | 8/2017 | |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Avimer, Wikipedia, Wikimedia Foundation, pp. 1-2 (2019).
Butte et al., "Interaction of Human PD-L1 and B7-1," *Mol Immunol.*, 45(13):3567-3572 (2008).
DARPin, Wikipedia, Wikimedia Foundation, pp. 1-4 (2019).
Heng et al., "Making cell-permeable antibodies (Transbody) through fusion of protein transduction domains (PTD) with single chain variable fragment (scFv) antibodies: potential advantages over antibodies expressed within the intracellular environment (Intrabody)," *Med Hypotheses*, 64(6):1105-1108 (2005).
Holtet et al., "Tetranectin, a trimeric plasminogen-binding C-type lectin," *Protein Science*, 6:1511-1515 (1997).
Lipovsek, "Adnectins: engineered target-binding protein therapeutics," *Protein Engineering, Design & Selection*, 24(1-2):3-9 (2011).

(Continued)

*Primary Examiner* — Nelson B Moseley, II
(74) *Attorney, Agent, or Firm* — Arnold & Porter Kaye Scholer

(57) ABSTRACT

The present invention relates to anti-PD-L1 binding members and in particular to monovalent, high potency PD-L1-binding antibody fragments being highly stable and soluble. Such binding members may be used in the treatment of cancer and inflammatory diseases as well as in diagnostics. Also provided are related nucleic acids, vectors, cells, and compositions.

18 Claims, 8 Drawing Sheets

Specification includes a Sequence Listing.

(56) References Cited

OTHER PUBLICATIONS

Moore et al., "Knottins: disulfide-bonded therapeutic and diagnostic peptides," *ScienceDirect*, 9(1):e3-e11 (2012).
Alfthan et al., "Properties of a single-chain antibody containing different linker peptides," *Protein Eng.* 8(7):725 (1995).
Berghoff et al., "PD1 (CD279) and PD-L1 (CD274, B7H1) expression in primary central nervous system lymphomas (PCNSL)", *Clinical Neurogathology* 33(1):42-9 (2014).
Black et al., "Activation of the PD-1/PD-L1 immune checkpoint confers tumor cell chemoresistance associated with increased metastasis," *Oncotarget* 7(9):10557-67 (2015).
Bodhankar et al., "PD-L1 Monoclonal Antibody Treats Ischemic Stroke by Controlling Central Nervous System Inflammation," *Stroke* 46(10): 2926-34 (2015).
Borras et al., "Generic approach for the generation of stable humanized single-chain FV fragments from rabbit monoclonal antibodies," *JBC* 285(12):9054 (2010).
Butte et al, "Interaction of human PD-L1 and B7-1", *Molecular Immunology*, (13):3567-3572 (2008).
Butte et al., "PD-L1 interacts specifically with B7-1 to inhibit T cell proliferation," *Immunity* 27:111-122 (2007).
Dimasi et al., "The design and characterization of oligospecific antibodies for simultaneous targeting of multiple disease mediators," *J. Mol. Biol.* 393:672-692 (2009).
Gilbreth et al., "Structural insights for engineering binding proteins based on non-antibody scaffolds," *Curr. Opin. Struct. Biol.* 22:413 (2012).
Ha et al., "Enhancing therapeutic vaccination by blocking PD-1-mediated inhibitory signals during chronic infection," *J Exp Med.* 205(3):543-55 (2008).
Haile et al., "Soluble CD80 Restores T Cell Activation and Overcomes Tumor Cell Programmed Death Ligand 1-Mediated Immune Suppression," *J Immunol.* 191(5): 2829-2836 (2013).
Haile et al., "Tumor Cell Programmed Death Ligand 1-Mediated T Cell Suppression Is Overcome by Coexpression of CD80," *J Immunol.* 186(12):6822-9 (2011).
He et al., "Development of PD-1/PD-L1 Pathway in Tumor Immune Microenvironment and Treatment for Non-Small Cell Lung Cancer," *Nature Scientific Reports* 5:13110 (2015).
Holliger et al., "Engineered antibody fragments and the rise of single domains," *Nature Biotechnol.* 23(9):1126 (2005).
Holliger et al., ""Diabodies": small bivalent and bispecific antibody fragments," *PNAS* 90(14):6444 (1993).
Honegger et al., "Yet another numbering scheme for immunoglobulin variable domains: An automatic modelling and analysis tool" *J. Mol. Biol.* 309:657 (2001).
Hossler, "Optimal and consistent protein glycosylation in mammalian cell culture," *Glycobiology*, 1 (9):936-949 (2009).
International Search Report issued in International Patent Application No. PCT/EP2017/054367 dated May 24, 2017.
Janakiram et al., "Immune checkpoint blockade in human cancer therapy: lung cancer and hematologic malignancies," Immunotherapy; 8(7):809-19 (2016).
Koestner er al., "PD-L1 blockade effectively restores strong graft-versus-leukemia effects without graft-versus-host disease after delayed adoptive transfer of T-cell receptor gene-engineered allogeneic $CD8^+T$ cells," *Blood* 117(3): 1030-1041 (2011).
Latchman et al., "PD-L2 is a second ligand for PD-1 and inhibits T cell activation," *Nat Immunol.* 2:261-8 (2001).
Maute et al., "Engineeiing high-affinity PD-1 vaiiants for optimized immunotherapy and immune-PET imaging," *PNAS* 112(47): E6506-E6514 (2015).
Needleman et al., "A general method applicable to the search for similarities in the amino acid sequence of two proteins," *J. Mol. Biol.* 48:443 (1970).
Nicholls et al., "Characterization of single-chain antibody (sFV)-toxin fusion proteins produced in vitro in rabbit reticulocyte lysate," *J. Biol Chem.* 268(7):5302-5308 (1993).
Pasut et al., "State of the art in PEGylation: the great versatility achieved after forty years of research," *J. Control Release* 161(2):461 (2012).
Rammes et al., "Identification of a Domain which Affects Kinetics and Antagonistic Potency of Clozapine at $5-HT_3$ Receptors," *PLOSONE* 4: 1-14 (2009).
Silverman et al., "Multivalent avimer proteins evolved by exon shuffling of a family of human receptor domains," *Nature Biotechnol.*, 23(12):1556 (2005).
Unverdorben et al., "Half-life extension of a single-chain diabody by fusion to domain B of staphylococcal protein A," *Protein Eng., Design & Selection* 25:81 (2012).
Zhen et al., "Concentration of receptor and ligand revisited in a modified receptor binding protocol for high-affinity radioligands: [3H] spiperone binding to D2 and D3 dopamine receptors," *J. Neurosci. Meth.* 188:32 (2010).

* cited by examiner

A

B

A

B

SEQUENCE LISTING

<160> NUMBER OF SEQ ID NOS: 27

<210> SEQ ID NO 1
<211> LENGTH: 114
<212> TYPE: PRT
<213> ORGANISM: Artificial Sequence
<220> FEATURE:
<223> OTHER INFORMATION: VL of scFv1

<400> SEQUENCE: 1

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asp Ile Tyr Ser Leu
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
            50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gly Asn Tyr Gly Ser Ser Ser
                85                  90                  95

Ser Ser Ser Tyr Gly Ala Val Phe Gly Gln Gly Thr Lys Leu Thr Val
            100                 105                 110

Leu Gly

<210> SEQ ID NO 2
<211> LENGTH: 120
<212> TYPE: PRT
<213> ORGANISM: Artificial Sequence
<220> FEATURE:
<223> OTHER INFORMATION: VH of scFv1

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Thr Val Ser Gly Ile Asp Leu Ser Ser Tyr
            20                  25                  30

Thr Met Gly Trp Val Arg Gln Ala Pro Gly Lys Gly Leu Glu Trp Val
        35                  40                  45

Gly Ile Ile Ser Ser Gly Gly Arg Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Thr Gly Tyr Pro Tyr Tyr Phe Ala Leu Trp Gly Gln
            100                 105                 110

Gly Thr Leu Val Thr Val Ser Ser
        115                 120

<210> SEQ ID NO 3
<211> LENGTH: 11
<212> TYPE: PRT
<213> ORGANISM: Oryctolagus cuniculus

<400> SEQUENCE: 3

Gln Ala Ser Glu Asp Ile Tyr Ser Leu Leu Ala
1               5                   10

<210> SEQ ID NO 4
<211> LENGTH: 7
<212> TYPE: PRT
<213> ORGANISM: Oryctolagus cuniculus

<400> SEQUENCE: 4

Asp Ala Ser Asp Leu Ala Ser
1               5

<210> SEQ ID NO 5
<211> LENGTH: 15
<212> TYPE: PRT
<213> ORGANISM: Oryctolagus cuniculus

```
<400> SEQUENCE: 5

Gln Gly Asn Tyr Gly Ser Ser Ser Ser Tyr Gly Ala Val
1               5                   10                  15

<210> SEQ ID NO 6
<211> LENGTH: 9
<212> TYPE: PRT
<213> ORGANISM: Oryctolagus cuniculus

<400> SEQUENCE: 6

Ile Asp Leu Ser Ser Tyr Thr Met Gly
1               5

<210> SEQ ID NO 7
<211> LENGTH: 16
<212> TYPE: PRT
<213> ORGANISM: Oryctolagus cuniculus

<400> SEQUENCE: 7

Ile Ile Ser Ser Gly Gly Arg Thr Tyr Tyr Ala Ser Trp Ala Lys Gly
1               5                   10                  15

<210> SEQ ID NO 8
<211> LENGTH: 12
<212> TYPE: PRT
<213> ORGANISM: Oryctolagus cuniculus

<400> SEQUENCE: 8

Gly Arg Tyr Thr Gly Tyr Pro Tyr Tyr Phe Ala Leu
1               5                   10

<210> SEQ ID NO 9
<211> LENGTH: 254
<212> TYPE: PRT
<213> ORGANISM: Artificial Sequence
<220> FEATURE:
<223> OTHER INFORMATION: scFv1

<400> SEQUENCE: 9

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asp Ile Tyr Ser Leu
                20                  25                  30

Leu Ala Trp Tyr Gln Gln Lys Pro Gly Lys Ala Pro Lys Leu Leu Ile
            35                  40                  45

Tyr Asp Ala Ser Asp Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gly Asn Tyr Gly Ser Ser Ser
                85                  90                  95

Ser Ser Ser Tyr Gly Ala Val Phe Gly Gln Gly Thr Lys Leu Thr Val
                100                 105                 110

Leu Gly Gly Gly Gly Gly Ser Gly Gly Gly Ser Gly Gly Gly Gly
            115                 120                 125

Ser Gly Gly Gly Gly Ser Glu Val Gln Leu Val Glu Ser Gly Gly Gly
        130                 135                 140

Leu Val Gln Pro Gly Gly Ser Leu Arg Leu Ser Cys Thr Val Ser Gly
145                 150                 155                 160
```

```
Ile Asp Leu Ser Ser Tyr Thr Met Gly Trp Val Arg Gln Ala Pro Gly
            165                 170                 175

Lys Gly Leu Glu Trp Val Gly Ile Ile Ser Ser Gly Gly Arg Thr Tyr
        180                 185                 190

Tyr Ala Ser Trp Ala Lys Gly Arg Phe Thr Ile Ser Arg Asp Thr Ser
        195                 200                 205

Lys Asn Thr Val Tyr Leu Gln Met Asn Ser Leu Arg Ala Glu Asp Thr
        210                 215                 220

Ala Val Tyr Tyr Cys Ala Arg Gly Arg Tyr Thr Gly Tyr Pro Tyr Tyr
225                 230                 235                 240

Phe Ala Leu Trp Gly Gln Gly Thr Leu Val Thr Val Ser Ser
                245                 250
```

```
<210> SEQ ID NO 10
<211> LENGTH: 20
<212> TYPE: PRT
<213> ORGANISM: Artificial Sequence
<220> FEATURE:
<223> OTHER INFORMATION: linker

<400> SEQUENCE: 10

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 11
<211> LENGTH: 255
<212> TYPE: PRT
<213> ORGANISM: Artificial Sequence
<220> FEATURE:
<223> OTHER INFORMATION: methylated scFv1

<400> SEQUENCE: 11

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Asp Ile Tyr Ser
            20                  25                  30

Leu Leu Ala Trp Tyr Gln Gln Lys Pro Gly Lys Ala Pro Lys Leu Leu
        35                  40                  45

Ile Tyr Asp Ala Ser Asp Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Gly Asn Tyr Gly Ser Ser
                85                  90                  95

Ser Ser Ser Ser Tyr Gly Ala Val Phe Gly Gln Gly Thr Lys Leu Thr
            100                 105                 110

Val Leu Gly Gly Gly Gly Ser Gly Gly Gly Gly Ser Gly Gly Gly Gly
        115                 120                 125

Gly Ser Gly Gly Gly Gly Ser Glu Val Gln Leu Val Glu Ser Gly Gly
    130                 135                 140

Gly Leu Val Gln Pro Gly Gly Ser Leu Arg Leu Ser Cys Thr Val Ser
145                 150                 155                 160

Gly Ile Asp Leu Ser Ser Tyr Thr Met Gly Trp Val Arg Gln Ala Pro
                165                 170                 175

Gly Lys Gly Leu Glu Trp Val Gly Ile Ile Ser Ser Gly Gly Arg Thr
            180                 185                 190
```

```
Tyr Tyr Ala Ser Trp Ala Lys Gly Arg Phe Thr Ile Ser Arg Asp Thr
            195                 200                 205

Ser Lys Asn Thr Val Tyr Leu Gln Met Asn Ser Leu Arg Ala Glu Asp
        210                 215                 220

Thr Ala Val Tyr Tyr Cys Ala Arg Gly Arg Tyr Thr Gly Tyr Pro Tyr
225                 230                 235                 240

Tyr Phe Ala Leu Trp Gly Gln Gly Thr Leu Val Thr Val Ser Ser
                245                 250                 255

<210> SEQ ID NO 12
<211> LENGTH: 23
<212> TYPE: PRT
<213> ORGANISM: Artificial Sequence
<220> FEATURE:
<223> OTHER INFORMATION: VL FR1

<400> SEQUENCE: 12

Glu Ile Val Met Thr Gln Ser Pro Ser Thr Leu Ser Ala Ser Val Gly
1               5                   10                  15

Asp Arg Val Ile Ile Thr Cys
            20

<210> SEQ ID NO 13
<211> LENGTH: 15
<212> TYPE: PRT
<213> ORGANISM: Artificial Sequence
<220> FEATURE:
<223> OTHER INFORMATION: VL FR2

<400> SEQUENCE: 13

Trp Tyr Gln Gln Lys Pro Gly Lys Ala Pro Lys Leu Leu Ile Tyr
1               5                   10                  15

<210> SEQ ID NO 14
<211> LENGTH: 32
<212> TYPE: PRT
<213> ORGANISM: Artificial Sequence
<220> FEATURE:
<223> OTHER INFORMATION: VL FR3

<400> SEQUENCE: 14

Gly Val Pro Ser Arg Phe Ser Gly Ser Gly Ser Gly Ala Glu Phe Thr
1               5                   10                  15

Leu Thr Ile Ser Ser Leu Gln Pro Asp Asp Phe Ala Thr Tyr Tyr Cys
                20                  25                  30

<210> SEQ ID NO 15
<211> LENGTH: 11
<212> TYPE: PRT
<213> ORGANISM: Artificial Sequence
<220> FEATURE:
<223> OTHER INFORMATION: VL FR4

<400> SEQUENCE: 15

Phe Gly Gln Gly Thr Lys Leu Thr Val Leu Gly
1               5                   10

<210> SEQ ID NO 16
<211> LENGTH: 26
<212> TYPE: PRT
<213> ORGANISM: Artificial Sequence
<220> FEATURE:
<223> OTHER INFORMATION: VH FR1
```

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Thr Val Ser Gly
            20                  25

<210> SEQ ID NO 17
<211> LENGTH: 14
<212> TYPE: PRT
<213> ORGANISM: Artificial Sequence
<220> FEATURE:
<223> OTHER INFORMATION: VH FR2

<400> SEQUENCE: 17

Trp Val Arg Gln Ala Pro Gly Lys Gly Leu Glu Trp Val Gly
1               5                   10

<210> SEQ ID NO 18
<211> LENGTH: 32
<212> TYPE: PRT
<213> ORGANISM: Artificial Sequence
<220> FEATURE:
<223> OTHER INFORMATION: VH FR3

<400> SEQUENCE: 18

Arg Phe Thr Ile Ser Arg Asp Thr Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 19
<211> LENGTH: 11
<212> TYPE: PRT
<213> ORGANISM: Artificial Sequence
<220> FEATURE:
<223> OTHER INFORMATION: VH FR4

<400> SEQUENCE: 19

Trp Gly Gln Gly Thr Leu Val Thr Val Ser Ser
1               5                   10

<210> SEQ ID NO 20
<211> LENGTH: 450
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Thr Val Ser Gly Ile Asp Leu Ser Ser Tyr
            20                  25                  30

Thr Met Gly Trp Val Arg Gln Ala Pro Gly Lys Gly Leu Glu Trp Val
        35                  40                  45

Gly Ile Ile Ser Ser Gly Gly Arg Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Thr Gly Tyr Pro Tyr Tyr Phe Ala Leu Trp Gly Gln
            100                 105                 110

```
Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 21
<211> LENGTH: 448
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30
```

```
Trp Ile His Trp Val Arg Gln Ala Pro Gly Lys Gly Leu Glu Trp Val
         35                  40                  45

Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 22
<211> LENGTH: 451
<212> TYPE: PRT
<213> ORGANISM: Homo sapiens

<400> SEQUENCE: 22

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Arg | Tyr |
| | | | 20 | | | | | 25 | | | | | 30 | | |
| Trp | Met | Ser | Trp | Val | Arg | Gln | Ala | Pro | Gly | Lys | Gly | Leu | Glu | Trp | Val |
| | | 35 | | | | | 40 | | | | | 45 | | | |
| Ala | Asn | Ile | Lys | Gln | Asp | Gly | Ser | Glu | Lys | Tyr | Tyr | Val | Asp | Ser | Val |
| 50 | | | | | 55 | | | | | 60 | | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Glu | Gly | Gly | Trp | Phe | Gly | Glu | Leu | Ala | Phe | Asp | Tyr | Trp | Gly |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | 195 | | | | | 200 | | | | | 205 | | | |
| Lys | Pro | Ser | Asn | Thr | Lys | Val | Asp | Lys | Lys | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Leu | Leu | Gly |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Tyr | Asn | Ser | Thr | Tyr |
| | 290 | | | | | 295 | | | | | 300 | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Glu | Glu | Met | Thr | Lys | Asn | Gln | Val | Ser |
| | | 355 | | | | | 360 | | | | | 365 | | | |
| Leu | Thr | Cys | Leu | Val | Lys | Gly | Phe | Tyr | Pro | Ser | Asp | Ile | Ala | Val | Glu |
| | 370 | | | | | 375 | | | | | 380 | | | | |

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 23
<211> LENGTH: 450
<212> TYPE: PRT
<213> ORGANISM: Mus musculus

<400> SEQUENCE: 23

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Arg Gly Leu Glu Trp Val
        35                  40                  45

Ser Gly Ile His Trp His Gly Lys Arg Thr Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Lys Gly Glu Asp Thr Ala Leu Tyr His Cys
                85                  90                  95

Val Arg Gly Gly Met Ser Thr Gly Asp Trp Phe Asp Pro Trp Gly Gln
            100                 105                 110

Gly Thr Leu Val Ile Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

```
Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Met Thr Lys Lys Gln Val Thr Leu
        355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 24
<211> LENGTH: 220
<212> TYPE: PRT
<213> ORGANISM: Homo sapiens

<400> SEQUENCE: 24

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Asp Ile Tyr Ser Leu
            20                  25                  30

Leu Ala Trp Tyr Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gly Asn Tyr Gly Ser Ser Ser
                85                  90                  95

Ser Ser Ser Tyr Gly Ala Val Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 25
<211> LENGTH: 214
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 215
<212> TYPE: PRT
<213> ORGANISM: Homo sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 215
<212> TYPE: PRT
<213> ORGANISM: Mus musculus

<400> SEQUENCE: 27

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

BINDING MEMBERS TO PD-L1

FIELD OF THE INVENTION

Provided is a binding member against PD-L1, such as a humanized antibody fragment, in particular a monovalent, highly potent and stable anti-PD-L1 scFv, applicable for therapeutic and diagnostic uses. Provided is also a nucleic acid molecule encoding such a binding member, a vector containing the sequence of a respective nucleic acid molecule, a host cell containing the vector or the nucleic acid sequence of a respective nucleic acid molecule, a pharmaceutical and a diagnostic composition containing the binding member or the nucleic acid molecule, as well as a use thereof.

BACKGROUND

Programmed cell death protein 1 (PD-1) is a cell surface receptor expressed on activated T cells, B cells and myeloid cells. PD-1 binds two ligands, PD-L1 (Dong H, et al. Nat Med. 1999; 5:1365-1369) and PD-L2 (Latchman Y. et al Nat Immunol. 2001; 2:261-8).

Upon binding of either ligand PD-L1 or PD-L2 to PD-1, an inhibitory signalling cascade is triggered within the T cell which inhibits TCR-mediated activation of IL-2 production and T cell proliferation. PD-L1 (programmed death-ligand 1) is a type 1 transmembrane protein which is constitutively expressed or induced by IFNγ on the surface of most human cancer cells and antigen presenting cells (APCs).

Further to PD-1, PD-L1 binds to CD80 (Butte M. J. et al (2007) 27:111-122), a membrane receptor that is capable of binding CD28 and CTLA-4. However, PD-L1 interacts more strongly with PD-1 than with CD80. Like PD-1, CD80 is a membrane receptor expressed on T cells and B cells. PD-L1 binding to either PD-1 or CD80 transmits inhibitory signals to T-lymphocytes, suppressing T-cell migration, proliferation and secretion of cytotoxic mediators, and reducing tumor cell killing. However, while PD-1/PD-L1 interaction drives T cell exhaustion, PD-L1/CD80 interaction drives T cell anergy. These are distinct processes as exhaustion is progressive over a period of weeks or months and depends on the chronic antigen stimulus, while anergy is induced rapidly after antigen stimulation in the absence of appropriate costimulation.

Consequently, PD-L1 expression protects tumor cells from T cell-mediated destruction (Haile S. T. et al (2011), J Immunol.; 186(12):6822-9; Haile S. T. et al (2013), J Immunol.; 191(5): 2829-2836). Up-regulated levels of PD-L1 correlate with increased tumor aggressiveness and an increased risk of death. Animal studies demonstrated that blocking of the PD-L1:PD-1 interaction via monoclonal antibodies improves T cell activation and reduces tumor progression. Moreover, antibody blocking of PD-L1 signalling through T cell-expressed CD80 prevents T cell anergy.

Monoclonal antibodies that block either PD-1 or PD-L1 have demonstrated impressive activity across a broad set of cancer subtypes, even at advanced and metastatic stages of disease (Maute et al (2015), PNAS, 112(47): E6506-E6514). Although earlier studies suggested that blockade of PD-L1 interactions with PD-1 or CD80 alone may be more beneficial, in terms of augmenting immunity while minimizing the risk of immunopathology (Butte M J (2008), Mol Immunol; 45(13):3567-72), recent clinical trials with monoclonal antibodies blocking PD-L1 interaction with both PD-1 and CD80 showed notable clinical success in several cancers and they are less toxic than traditional chemotherapy. Although only a subset of patients respond to checkpoint blockade, the duration of such response due to immunological memory is remarkable and is longer than would be expected with any other agent in refractory disease (Janakiram M et al (2016), Immunotherapy; 8(7):809-19).

Atezolizumab (MPDL3280A, e.g., described in U.S. Pat. No. 8,217,149) is a humanized IgG1 antibody targeting PD-L1 such that receptor binding to PD-1 and CD80 is blocked. The antibody was engineered to have a reduced Fc-effector function and therewith reduced depletion of cells expressing PD-L1. In October 2016, the FDA approved atezolizumab for the treatment of patients with metastatic non-small cell lung cancer (NSCLC) who have disease progression during or following platinum-containing chemotherapy. If the tumor has EGFR or ALK genomic aberrations, patients should have disease progression on FDA-approved therapy for these aberrations prior to receiving the antibody. The underlying clinical studies enrolled patients regardless of their PD-L1 status and included both squamous and non-squamous disease types. In May 2016, the FDA approved atezolizumab for the treatment of patients with locally advanced or metastatic urothelial carcinoma, who have disease progression during or following platinum containing chemotherapy.

Durvalumab (MEDI4736; see, e.g., U.S. Pat. No. 8,779,108, WO2010077634) is a human IgG1 monoclonal anti-PD-L1 antibody that blocks both PD-1 and CD80 interaction upon PD-L1 binding. The antibody was generated by immunizing IgG2 and IgG4 XenoMouse animals and exchanging the constant domain for a human IgG1 triple-mutant domain. This constant domain contains three point mutations that reduce binding to C1q and the Fc gamma receptors, resulting in reduced antibody-dependent cellular cytotoxicity and complement-dependent cytotoxicity.

The antibody is in clinical trials as a monotherapy for a number of indications, including locally advanced or metastatic NSCLC, urothelial cancer, Head and Neck Cancer, cervical, colorectal, esophageal, ovarian, breast, SCLC and gastric cancers and recurrent or metastatic PD-L1-positive Squamous Cell Carcinoma of the Head and Neck (SCCHN). Combination therapy clinical trials are ongoing.

A further antibody targeting PD-1 and blocking both PD-1 and CD80 interaction with PD-L1 is avelumab (MSB0010718C, described in WO2013079174). The fully human IgG1 monoclonal antibody retains a native Fc-region and may therefore induce antibody-dependent cell-mediated cytotoxicity (ADCC). The antibody is in clinical trials for solid tumors, gastric cancers, Merkel cell carcinoma, and NSCLC.

There is still the need for improved compounds targeting immune checkpoint inhibitors and to provide safe and effective therapeutic methods to treat immune system-related disorders, such as cancer, immune deficiency, autoimmune diseases, allergies, inflammatory disorders, transplant rejection, and other disorders.

SUMMARY OF THE INVENTION

The present invention provides for binding members binding PD-L1, including nucleic acids and vectors encoding, host cells expressing and compositions containing such binding members as well as for their use in therapy.

Such a binding member has one or more of the following properties:

(a) has high affinity to PD-L1, both as immunoglobulin as well as in a monovalent antibody fragment format such as an scFv.

(b) binds human PD-L1 with a binding dissociation equilibrium constant (KD) of lower than 10 pM as measured by Kinetic Exclusion Assay under the conditions indicated in Example 4 for the monovalent or the conditions indicated in Example 9 for the bivalent format;

(c) binds to an epitope on PD-L1 which impedes human PD-L1 interaction with both human PD-1 and human CD80;

(d) cross-reacts with monkey PD-L1;

(e) binds monkey PD-L1, with a binding affinity at least as strong, more preferably at least twice as strong for monkey PD-L1 as for human PD-L1;

(f) does not bind to human PD-L2 or human B7-H3;

(g) inhibits tumor growth in an HCC827 human lung cancer model; and (h) forms less than 3% of dimers after 1 or 2 weeks of storage at 37° C. at a concentration of 10 mg/ml in PBS at pH 7.2 in the scFv format.

Such binding members preferably comprise (i) at least one of the variable heavy chain CDR-H1, CDR-H2 and CDR-H3 sequences as set forth in SEQ ID NOs: 6, 7 and 8, respectively; and/or (ii) at least one of the variable light chain CDR-L1, CDR-L2 and CDR-L3 sequences as set forth in SEQ ID NOs: 3, 4 and 5, respectively; or a variant thereof.

Such binding members may be used in the treatment of cancer and inflammatory diseases as well as in diagnostics. Also provided are related nucleic acids, vectors, cells, compositions, methods and kits.

DETAILED DESCRIPTION

Figure 1:
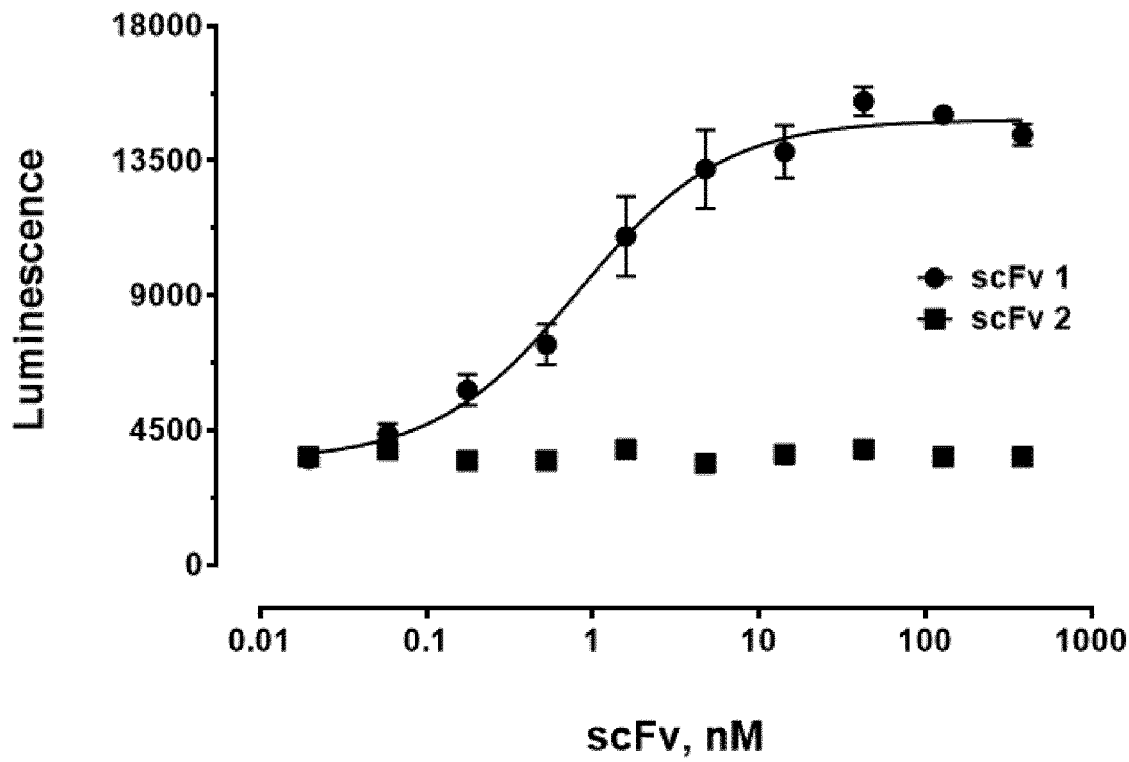
FIG. 1 shows that scFv1 blocks the recombinant human (rh) PD-L1 and rhPD-1 mediated immune checkpoint inhibitory signal in a cell based system.

In order that the explanations on the binding members, nucleic acids, vectors, host cells, compositions, methods and uses disclosed herein may be more readily understood, certain terms are first defined.

Definitions

Unless otherwise defined, all other scientific and technical terms used in the description, figures and claims have their ordinary meaning as commonly understood by one of ordinary skill in the art. Although similar or equivalent methods and materials to those described herein can be used in the practice or testing of the binding members, nucleic acids, vectors, host cells, compositions, methods and uses disclosed herein, suitable methods and materials are described below. All publications, patent applications, patents, and other references mentioned herein are incorporated by reference in their entirety. In case of conflict, the present specification, including definitions, will prevail. The materials, methods, and examples are illustrative only and not intended to be limiting.

The term "administering", as used herein, refers to any mode of transferring, delivering, introducing, or transporting matter such as a compound, e.g. a pharmaceutical compound, or other agent such as an antigen, to a subject. Modes of administration include, without being limited to, parenteral administration, oral, rectal, systemic, intravenous, subcutaneous, urogenital, topical, intravitreal, intraocular, otic, intranasal, transdermal, intradermal, dermal, intraperitoneal, intramuscular, sublingual, or buccal administration. Administration "in combination with" further matter such as one or more therapeutic agents includes simultaneous (concurrent) and consecutive administration in any order.

As used herein, the terms "conservative modification" and "conservative substitution" refer to a modification and a substitution, respectively, that maintains physically, biologically, chemically and/or functionally the properties with regard to the corresponding reference. A molecule that includes a sequence with conservative substitution for instance has a similar size, shape, electric charge, chemical properties, including a comparable ability to form covalent or hydrogen bonds, and/or comparable polarity. Such conservative modifications include, but are not limited to, one or more nucleobases and amino acid substitutions, additions and deletions.

For example, conservative amino acid substitutions include those in which the amino acid residue is replaced with an amino acid residue having a similar side chain. For example, amino acid residues being non-essential with regard to binding to an antigen can be replaced with another amino acid residue from the same side chain family, e.g. serine may be substituted for threonine. Amino acid residues are usually divided into families based on common, similar side-chain properties, such as:
1. nonpolar side chains (e.g., glycine, alanine, valine, leucine, isoleucine, methionine),
2. uncharged polar side chains (e.g., asparagine, glutamine, serine, threonine, tyrosine, proline, cysteine, tryptophan), 3. basic side chains (e.g., lysine, arginine, histidine, proline),
4. acidic side chains (e.g., aspartic acid, glutamic acid),
5. beta-branched side chains (e.g., threonine, valine, isoleucine) and
6. aromatic side chains (e.g., tyrosine, phenylalanine, tryptophan, histidine).

A conservative substitution can be taken to be a substitution of a first amino acid within one of the six groups above by a further amino acid within the same group of the six groups. Preferred conservative substitutions include:
1. Substituting alanine (A) by valine (V);
2. Substituting arginine (R) by lysine (K);
3. Substituting asparagine (N) by glutamine (Q);
4. Substituting aspartic acid (D) by glutamic acid (E);
5. Substituting cysteine (C) by serine (S);
6. Substituting glutamic acid (E) by aspartic acid (D);
7. Substituting glycine (G) by alanine (A);
8. Substituting histidine (H) by arginine (R) or lysine (K);
9. Substituting isoleucine (I) by leucine (L);
10. Substituting methionine (M) by leucine (L);
11. Substituting phenylalanine (F) by tyrosine (Y);
12. Substituting serine (S) by threonine (T);
13. Substituting tryptophan (W) by tyrosine (Y);
14. Substituting phenylalanine (F) by tryptophan (W); and/or
15. Substituting valine (V) by leucine (L)

and vice versa. Other substitutions such as substituting proline (P) by alanine (A) are also permissible and can be determined empirically or in accord with other known conservative or non-conservative substitutions. A conservative substitution may also involve the use of a non-natural amino acid.

Non-conservative substitutions, i.e. exchanging members of one family against members of another family, may lead to substantial changes, e.g. with respect to the charge, dipole moment, size, hydrophilicity, hydrophobicity or conformation of the binding member, which may alter the binding activity, in particular if amino acids are affected that are essential for binding to the target molecule. A non-conservative substitution may also involve the use of a non-natural amino acid.

Conservative and non-conservative modifications can be introduced into parental binding members by a variety of standard techniques known in the art, such as combinatorial chemistry, site-directed DNA mutagenesis, PCR-mediated and/or cassette mutagenesis, peptide/protein chemical synthesis, introducing appropriate modifications into or constructing a new nucleic acid sequence encoding the binding member and/or a chemical reaction specifically modifying reactive groups in the parental binding member. The variants can be tested by routine methods for their chemical, biological, biophysical and/or biochemical properties. Preferably, the conservative amino acid substitution does not substantially change the functional, and generally also the structural characteristics of the parental sequence. Accordingly, the binding characteristics of a binding member that includes a conservative substitution are at least essentially unaltered. Furthermore, a conservative amino acid substitution generally does not substantially modify or disrupt a secondary structure of the parental sequence.

The term "label" is used herein to refer to any substance the detection or measurement of which, either directly or indirectly, by physical or chemical means, is indicative of the presence of a selected target bioentity in a sample. Representative examples of useful detectable labels include, but are not limited to, molecules or ions directly or indirectly detectable based on light absorbance, fluorescence, reflectivity, light scatter, phosphorescence, or luminescence properties, molecules or ions detectable by their radioactive properties or molecules or ions detectable by their nuclear magnetic resonance or paramagnetic properties. A label may in some embodiments be a molecule that can be indirectly detected based on light absorbance or fluorescence, for example, various enzymes which cause appropriate substrates to convert, e.g., from non-light absorbing to light absorbing molecules, or from non-fluorescent to fluorescent molecules.

An "effective amount" or a "therapeutically effective amount" of an item such as a compound, including a binding member disclosed herein, is an amount—either as a single dose or as part of a series of doses—which at the dosage regimen applied yields the desired therapeutic effect, i.e., to reach a certain treatment goal. A therapeutically effective amount is generally an amount sufficient to provide a therapeutic benefit in the treatment or management of the relevant pathological condition, or to delay or minimize one or more symptoms associated with the presence of the condition. The dosage will depend on various factors including patient and clinical factors (e.g., age, weight, gender, clinical history of the patient, severity of the disorder and/or response to the treatment), the nature of the disorder being treated, the particular composition to be administered, the route of administration, and other factors.

The term "essentially consists of" is understood to allow the presence of additional components in a sample or a composition that do not affect the properties of the sample or a composition. As an illustrative example, a pharmaceutical composition may include excipients if it essentially consists of an active ingredient.

Within the scope of the present disclosure, the term "antibody" refers to a full-length immunoglobulin as well as to fragments thereof. Such a full-length immunoglobulin may be monoclonal, polyclonal, chimeric, humanized, veneered and/or a human antibody. A chimeric antibody may e.g. include a constant region of a different species and/or a different isotype or be an artificial bispecific or multispecific construct, such as e.g. a quadroma, a knob-into-hole (KIH) or CrossMab or a DuoBody. The term also encompasses constructs where full-length immunoglobulins are fused to an antibody fragment or a non-antibody scaffold. Exemplary examples thereof, without being limited to, include Bs1Ab, Bs2Ab, Bs3Ab, Bs4Ab, Ts1Ab and Ts2Ab as described by Dimasi N. et al (2009), JMB 393, 672-692. Further chimeric antibodies include DVD-Ig, IgG-scFab, scFab-dsscFv, Fv2-Fc, scFv-KIH, FynomABs, or BiTE-KIH. An antibody as disclosed herein may in some embodiments be glycosylated in other embodiments, the antibody is not glycosylated.

By "fragment" in reference to a polypeptide such as an antibody or a proteinaceous binding molecule is meant any amino acid sequence present in a corresponding polypeptide, as long as it is shorter than the full-length immunoglobulin sequence and as long as it is capable of performing the function of interest of the protein—in the case of an antibody specifically binding to the desired target, e.g. antigen (such as PD-L1). The term "antibody fragment" refers to a portion of an antibody, often the hypervariable region and portions of the surrounding heavy and light chains, that displays specific binding affinity for a particular target, typically a molecule. A hypervariable region is a portion of an antibody that physically binds to the polypeptide target. An antibody fragment thus includes or consists of one or more portions of a full-length antibody retaining the targeting specificity of the antibody. Such antibody fragment may for instance lack at least partially the constant region (Fc region) of the full-length antibody. In some embodiments, an antibody fragment is produced by digestion of the full-length antibody. An antibody fragment may also be a synthetic or recombinant construct that contains one or more parts of the antibody (see e.g., Holliger P and Hudson J. Engineered antibody fragments and the rise of single domains. *Nature Biotechnol.* 2005, vol. 23, 9, p. 1126). Examples of an antibody fragment include, but are not limited to, an scFv, a Fab, a Fv, a Fab', a F(ab')$_2$ fragment, a scFab, a dAb, a VHH, a nanobody, a V(NAR) or a so called minimal recognition unit, a diabody, a single-chain diabody (scDb), a tandem scDb (Tandab), a linear dimeric scDb (LD-scDb), a circular dimeric scDb (CD-scDb), a BiTE (also called bispecific T-cell engager, tandem scFv or tandem di-scFv), a DART, a tandem tri-scFv, a tri(a)body, bispecific Fab2, di-miniantibody, tetrabody, di-diabody, or scFab-dsscFv.

A "single chain variable fragment" or a "single chain antibody" or a "scFv" are examples of a type of antibody fragment. A scFv is a fusion protein that includes the VH and VL domains of an antibody connected by a linker. It thus lacks the constant Fc region which is present in a full-length antibody.

A "binding member" as used herein refers to a proteinaceous binding molecule comprising one or more CDRs and optionally the variable light and/or heavy chains as disclosed herein. As such, the term "binding member" comprises antibodies (i.e. full-length immunoglobulins and antibody fragments as defined above), proteinaceous non-antibody scaffolds and/or other binding compounds. In some embodiments, the non-antibody scaffolds comprise one or more CDR sequences as disclosed herein. Such binding member can be monovalent or multivalent, i.e. having one or more antigen binding sites. Non-limiting examples of monovalent binding members include scFv, Fab, scFab, dAb, VHH, V(NAR) (or a so called minimal recognition unit), DARPins, affilins and nanobodies. A multivalent binding member can have two, three, four or more antigen binding sites. Full-length immunoglobulins, F(ab')$_2$ fragments, bis-scFv (or tandem scFv or BiTE), DART, diabodies, scDb, DVD-Ig, IgG-scFab, scFab-Fc-scFab, IgG-scFv, scFv-Fc, scFv-fc-scFv, Fv2-Fc, FynomABs, quadroma, CrossMab, DuoBody, triabodies and tetrabodies are non-limiting examples of multivalent binding members; in the exemplary multivalent binding members, two binding sites are present, i.e. the binding member is bivalent. In some embodiments, the multivalent binding member is bispecific, i.e. the binding member is directed against two different targets or two different target sites on one target molecule. Bispecific antibodies are, e.g., reviewed in Muller D. and Kontermann R. E. Bispecific antibodies. Edited by Dübel S. Weinheim: Wiley-VCH, 2007. ISBN 3527314539. p. 345. In some embodiments, the multivalent binding member includes more than two, e.g., three or four different binding sites for three or four, respectively, different antigens. Such binding member is multivalent and multispecific, in particular tri- or tetra-specific, respectively.

"Non-antibody scaffolds" are antigen-binding polypeptides which are e.g. described in Fielder M. and Skerra A. Non-antibody scaffolds. Edited by Diibel S. Weinheim: Wiley-VCH, 2007. ISBN 3527314539. p. 467; or Gilbreth R. N. and Koide S. Structural insights for engineering binding proteins based on non-antibody scaffolds. *Curr. Opin. Struct. Biol.* 2012, vol. 22, p. 413. Non-limiting examples include affibodies, affilin molecules, AdNectins, muteins based on polypeptides of the lipocalin family (Anticalins®), DARPins, Knottins, Kunitz-type domains, Avimers, fynomers, Tetranectins and trans-bodies. Avimers contain so called A-domains that occur as strings of multiple domains in several cell surface receptors (Silverman J., et al., *Nature Biotechnol.* 2005, vol. 23, p. 1556). Tetranectins, derived from the respective human homotrimeric protein, likewise contain loop regions in a C-type lectin domain that can be engineered for desired binding (ibid.).

A binding member as disclosed herein may be PEGylated or hyperglycosylated if desired, see also below. In some embodiments, a binding member is a fusion protein of one of the exemplary proteinaceous binding molecules above and an albumin-binding domain, for instance an albumin-binding domain of streptococcal protein G. In some embodiments, a binding member is a fusion protein of an antibody fragment, such as a single-chain diabody, and an antibody binding domain, for instance a bacterial antibody binding domain. As an illustrative example, a single-chain diabody may be fused to domain B of staphylococcal protein A as described by Unverdorben et al. (*Protein Eng., Design & Selection,* 2012, vol. 25, p. 81).

The "IC$_{50}$" or "half-maximum inhibitory concentration" is a measure of antagonist potency and describes quantitatively the effectiveness of a compound to inhibit a biological or biochemical function. This value accordingly indicates how much of a certain item, such as a binding member, is needed to inhibit by 50% a certain biological or biochemical process or function. Although no direct indicator of affinity, the IC$_{50}$ and the values are correlated and can be determined via the Cheng-Prusoff equation (Cheng Y. and Prusoff W. H. Relationship between the inhibition constant (Ki) and the concentration of inhibitor which causes 50 percent inhibition (IC$_{50}$) of an enzymatic reaction. Biochem. Pharmacol. 1973, vol. 22, p. 3099; Rammes G., et al., *PLOSONE* 2009, vol. 4, p. 1-14; Zhen J., et al., Concentration of receptor and ligand revisited in a modified receptor binding protocol for high-affinity radioligands: [$^3$H] spiperone binding to D$_2$ and D$_3$ dopamine receptors. *J. Neurosci. Meth.* 2010, vol. 188, p. 32).

The term "framework" (FR) refers to the scaffold of the variable antibody domain, either the variable light chain (VL) or variable heavy chain (VH), embedding the respective CDRs. A VL and/or VH framework typically includes four framework sections, FR1, FR2, FR3 and FR4, flanking the CDR regions. Thus, as known in the art, a VL has the general structure: (FR-L1)-(CDR-L1)-(FR-L2)-(CDR-L2)-(FR-L3)-(CDR-L3)-(FR-L4), whereas a VH has the general structure: (FR-H1)-(CDR-H1)-(FR-H2)-(CDR-H2)-(FR-H3)-(CDR-H3)-(FR-H4).

The term "CDR" refers to the hypervariable regions of the antibody which mainly contribute to antigen binding. Typically, an antigen binding site includes six CDRs, embedded into a framework scaffold. Herein, the CDRs of the VL are referred to as CDR-L1, CDR-L2 and CDR-L3 whereas the CDRs of the VH are referred to as CDR-H1, CDR-H2 and CDR-H3. These can be identified as described in KABAT, E. A., et al. Sequences of Proteins of Immunological Interest. 5th edition. Edited by U.S. DEPARTMENT OF HEALTH AND HUMAN SERVICES. NIH Publications, 1991. p. 91-3242. CDR-H1 as used herein, however, differs from the Kabat definition in that it starts with position 27 and ends prior to position 36 (AHo positions 28 to 42, inclusive).

As used herein, the numbering system to identify amino acid residue positions in the VH and VL of the antibody corresponds to the "AHo"-system described by Honegger A. and Plückthun A. Yet another numbering scheme for immunoglobulin variable domains: An automatic modelling and analysis tool. *J. Mol. Biol.* 2001, vol. 309, p. 657. The publication further provides conversion tables between the AHo and the Kabat system (Kabat E. A. et al., Sequences of Proteins of Immunological Interest. 5$^{th}$ edition. Edited by U.S. Department of Health and Human Services. NIH Publications, 1991. No. 91-3242).

"Humanized" antibodies refer to antibodies that include one or more, typically all six CDR regions of a non-human parent antibody or variants thereof or synthetic CDRs, and of which the framework is, e.g., (i) a human framework, potentially including one or more framework residues of the non-human parent antibody, or (ii) a framework from a non-human antibody modified to increase similarity to naturally produced human frameworks. Methods of humanizing antibodies are known in the art, e.g. Leger O., and Saldanha J. Antibody Drug Discovery. Edited by Wood C. London: Imperial College Press, 2011. ISBN 1848166281. p. 1-23.

The term "isolated" indicates that matter such as a peptide, a nucleic acid molecule or a cell has been removed from its normal physiological environment, e.g. a natural source, or that a peptide or nucleic acid is synthesized. Use of the term "isolated" indicates that a naturally occurring sequence has been removed from its normal cellular (e.g., chromosomal) environment. Thus, the sequence may be in a cell-free solution or placed in a different cellular environment. "Isolated" in reference to a polypeptide or nucleic acid molecule means a polymer of two or more amino acids or nucleotides coupled to each other, including a polypeptide or nucleic acid molecule that is isolated from a natural source or that is synthesized. The term "isolated" does not imply that the sequence is the only amino acid chain or nucleotide chain present, but that it is essentially free of, e.g., non-amino acid material and/or non-nucleic acid material, respectively, naturally associated with it. An "isolated cell" refers to a cell that is separated from the molecular and/or cellular components that naturally accompany the cell.

The term "identity" as used herein refers to the sequence match between two proteins or nucleic acids. The protein or nucleic acid sequences to be compared are aligned for maximum correspondence over a comparison window, for example using bioinformatics tools such as EMBOSS Needle (pair wise alignment; available at www.ebi.ac.uk or by manual alignment and visual inspection. When the same position in the sequences to be compared is occupied by the same nucleobase or amino acid residue, then the respective molecules are identical at that very position. Accordingly, the "percent identity" is a function of the number of matching positions divided by the number of positions compared and multiplied by 100%. For instance, if 6 out of 10 sequence positions are identical, then the identity is 60%. Aligning sequences for maximum correspondence may require introducing gaps. The percent identity between two protein sequences can, e.g., be determined using the Needleman and Wunsch algorithm (Needlemann S. B. and Wunsch C. D. A general method applicable to the search for similarities in the amino acid sequence of two proteins. *J. Mol. Biol.* 1970, vol. 48, p. 443) which has been incorporated into EMBOSS Needle, using a BLOSUM62 matrix, a "gap open penalty" of 10, a "gap extend penalty" of 0.5, a false "end gap penalty", an "end gap open penalty" of 10 and an "end gap extend penalty" of 0.5, or a method of aligning sequences manually introducing gaps in a manner which maximises identity can be used. Thus, in one embodiment, sequences disclosed herein are aligned by manually introducing gaps in a manner which maximises sequence identity. Two molecules having the same primary amino acid or nucleic acid sequence are identical irrespective of any chemical and/or biological modification. For example, two antibodies having the same primary amino acid sequence but different glycosylation patterns are identical by this definition. In case of nucleic acids, for example, two molecules having the same sequence but different linkage components such as thiophosphate instead of phosphate are identical by this definition. A sequence being longer than any of the sequences provided herein, for example because it comprises several variable domains or one or more constant domains, shall nevertheless be identical to the reference sequence disclosed herein if sequence identity over a comparison window is given. A comparison window as used herein includes the entire sequence as claimed. Similarly, nucleobases that differ only because of exocyclic modifications, for example cytosine and 5-methyl-cytosine, are identical by this definition.

The term "nucleic acid molecule" as used herein refers to any nucleic acid in any possible configuration, such as single stranded, double stranded or a combination thereof. Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules (e.g. Liu B. et al., *J. Am. Chem. Soc.* 2004, vol. 126, 4076). LNA has a modified RNA backbone with a methylene bridge between C4' and O2', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used in nucleic acids used in the methods disclosed in this specification. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

As used in this document, the expression "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "preventing" in the medical/physiological context, i.e. in the context of a physiological state, refers to decreasing the probability that an organism contracts or develops an abnormal condition.

"Similar" protein sequences are those which, when aligned, share similar amino acid residues and most often, but not mandatorily, identical amino acid residues at the same positions of the sequences to be compared. Similar amino acid residues are grouped by chemical characteristics of the side chains into families. These families are described above for "conservative amino acid substitutions". The "percent similarity" between sequences is the number of positions that contain identical or similar residues at the same sequence positions of the sequences to be compared divided by the total number of positions compared and multiplied by 100%. For instance, if 6 out of 10 sequence positions have identical amino acid residues and 2 out of 10 positions contain similar residues, then the sequences have 80% similarity. The similarity between two sequences can e.g. be determined using EMBOSS Needle. A sequence being longer than any of the sequences provided herein, for example because it comprises several variable domains or one or more constant domains, shall nevertheless be similar to the reference sequence disclosed herein if sequence similarity over a comparison window is given. A comparison window as used herein includes the entire sequence as claimed.

The term "specific" as used in this document is understood to indicate that a binding member or a binding compound binds to a defined target such as PD-L1 with an equilibrium binding constant $K_D$ of $<10^{-6}$ molar. This constant can be determined, e.g. using Quartz Crystal Microbalance (QCM) in an Attana instrument, Surface Plasmon Resonance (SPR) technology in a BIACORE instrument or Kinetic Exclusion Assay (KinExA®).

The terms "stratifying" and "stratification" as used herein indicate that an individual is assigned to a certain group according to characteristics matching the respective group such as a corresponding probability of responding to a binding member disclosed herein. The groups may be used, for example, for testing, prescribing, adjusting dosing, suspending or abandoning a binding member. Accordingly, in some embodiments of a method or use according to the invention a subject may be stratified into a subgroup of a clinical trial of a therapy.

The term "subject" as used herein, also addressed as an individual, refers to a human or non-human animal, generally a mammal. A subject may be a mammalian species such as a rabbit, a mouse, a rat, a guinea pig, a hamster, a dog, a cat, a pig, a cow, a goat, a sheep, a horse, a monkey, an ape or a human. Thus, the methods, uses and compositions described in this document are applicable to both human and veterinary disease. As explained in more detail below, the sample may be obtained from the subject. It is thus understood that conclusions drawn from expression levels in the sample and decisions based thereon concern the subject from whom/which the sample has been taken. Further, while a subject is typically a living organism, a method or use described in this document may also be used in post-mortem analysis. Where the subject is a living human who is receiving medical care for a disease or condition, it is also addressed as a "patient".

The terms "treatment" and "treating" as used herein, include a prophylactic or preventative measure having a therapeutic effect and/or preventing, slowing down (lessen), or at least partially alleviating or abrogating an abnormal, including pathologic, condition in the organism of a subject. Treatment according to the present disclosure involves the administration of a pharmaceutically effective amount of a molecule as described herein, i.e. inter alia, the binding member (such as an antibody), nucleic acid, vector or cell disclosed herein, to a subject in need thereof to prevent, cure, delay the onset and/or progression, reduce the severity of, stabilize, modulate, cure or ameliorate one or more symptoms of a PD-L1-related disorder. Typically, the binding member, nucleic acid, vector or host cell is provided in a pharmaceutical composition including those described herein. Those in need of treatment include those already with the disorder as well as those prone to having the disorder or those in whom the disorder is to be prevented (prophylaxis). Generally, a treatment reduces, stabilizes, or inhibits progression of a symptom that is associated with the presence and/or progression of a disease or pathological condition.

As used herein, "PD-L1" refers to the protein also known as "programmed cell death ligand 1," "cluster of differentiation 274 (i.e., CD274)" or "B7 homolog 1 (i.e., B7-H1)". The native protein comprises two extracellular domains, a transmembrane domain, and a cytoplasmic domain. The term encompasses full-length and/or unprocessed PD-L1 as well as any intermediate resulting from processing in the cell. PD-L1 can exist as a transmembrane protein or as a soluble protein; thus, the term as used herein may refer to the full length or the extracellular domain of the protein. The term also encompasses naturally occurring variants of PD-L1, e.g., splice variants or allelic variants. The protein may additionally contain a tag, such as a his tag or Fc tag. The amino acid sequence of exemplary human full-length PD-L1 protein can e.g. be found under NCBI protein database accession number NP_054862. The term "hPD-L1" refers to human PD-L1 and comprises natural hPD-L1 and recombinant human rhPD-L1. "rPD-L1" refers to recombinant PD-L1. Recombinant PD-L1 may or may not have an amino terminal methionine residue, depending upon the method by which it is prepared. "rhPD-L1" refers to recombinant human PD-L1. Likewise, PD-L1 may also be obtained by isolation from biological samples of human or non-human origin. rhPD-L1 may, e.g., be obtained from RnD Systems, USA, cat. no. 156-B7, or from Peprotech, USA, cat. no. 310-35. "Monkey PD-L1" refers to PD-L1 of Rhesus macacque (*Macaca mulatta*). The amino acid sequence of exemplary monkey PD-L1 protein can e.g. be found under NCBI protein database accession number NP_001077358. Monkey PD-L1 may, e.g., be obtained from Sino Biological, China, cat. no. 90251-C02H. "Rat PD-L1" refers to PD-L1 of *Rattus norvegicus* (Norway rat). The amino acid sequence of exemplary rat PD-L1 protein can e.g. be found under NCBI protein database accession number NP_001178883 Rat PD-L1 may, e.g., be obtained from Sino Biological, China, cat. no. 80450-R02H. "Mouse PD-L1" refers to PD-L1 of *Mus musculus*. The amino acid sequence of exemplary mouse PD-L1 protein can e.g. be found under NCBI protein database accession number NP_068693 Mouse PD-L1 may, e.g., be obtained from Sino Biological, China, cat. no. 50010-M03H or from RnD Systems, USA, cat. no. 1019-B7-100.

"PD-1" is the programmed cell death protein 1, also known as CD279 is a cell surface receptor for PD-L1. PD-1 binds two ligands, PD-L1 and PD-L2. PD-1 is a transmembrane protein including an extracellular domain followed by a transmembrane region and an intracellular domain. The term encompasses full-length and/or unprocessed PD-1 as well as any intermediate resulting from processing in the cell. PD-1 can exist as a transmembrane protein or as a soluble protein; thus, the term as used herein may refer to the full length or the extracellular domain of the protein. The term also encompasses naturally occurring variants of PD-1, e.g., splice variants or allelic variants. The protein may additionally contain a tag, such as a his tag or Fc tag. The amino acid sequence of exemplary human PD-1 protein can e.g. be found under NCBI protein database accession number NP_005009 The term "hPD-1" refers to human PD-1 and comprises its natural form (hPD-1) as well as the recombinant human form (rhPD-1). "rPD-1" refers to recombinant PD-1.

"CD80" refers to the cluster of differentiation 80, also known as B7-1, B7.1, BB1, CD28LG, CD28LG1, LAB7. It is a membrane receptor for CD28 and CTLA-4 as well as PD-L1 and comprises extracellular domain followed by a transmembrane region and an intracellular domain. The term encompasses full-length and/or unprocessed CD80 as well as any intermediate resulting from processing in the cell. CD80 can exist as a transmembrane protein or as a soluble protein; thus, the term as used herein may refer to the full length or the extracellular domain of the protein. The term also encompasses naturally occurring variants of CD80, e.g., splice variants or allelic variants. The protein may additionally contain a tag, such as a his tag or Fc tag. The amino acid sequence of exemplary human CD80 protein can e.g. be found under NCBI protein database accession number NP_005182. CD80 may, e.g., be obtained from RnD Systems, USA, cat. no. 9050-B1-100.". The term "hCD80" refers to human CD80 and comprises its natural form (hCD80) as well as the recombinant human form (rhCD80). "rCD80" refers to recombinant CD80.

"PD-L2" refers to the protein also known as "Programmed cell death 1 ligand 2", "B7-DC", or "CD273" (cluster of differentiation 273). The term as used herein encompasses full-length and/or unprocessed PD-L2 as well as any intermediate resulting from processing in the cell. PD-L2 can exist as a transmembrane protein or as a soluble protein; thus, the term as used herein may refer to the full length or the extracellular domain of the protein. The term also encompasses naturally occurring variants of PD-L2, e.g., splice variants or allelic variants. The protein may additionally contain a tag, such as a his tag or Fc tag. The amino acid sequence of exemplary human full-length PD-L2 protein can e.g. be found under NCBI protein database accession number NP_079515. PD-L2 may, e.g., be obtained from RnD Systems, USA, cat. no. 1224-PL. The term "rhPD-L2" refers to recombinant human PD-L2.

"B7-H3" refers to the protein also known as CD276 (Cluster of Differentiation 276). The term as used herein encompasses full-length and/or unprocessed B7-H3 as well as any intermediate resulting from processing in the cell. B7-H3 can exist as a transmembrane protein or as a soluble protein; thus, the term as used herein may refer to the full length or the extracellular domain of the protein. The term also encompasses naturally occurring variants of B7-H3, e.g., splice variants or allelic variants. The protein may additionally contain a tag, such as a his tag or Fc tag. The amino acid sequence of exemplary human full-length B7-H3 protein can e.g. be found under NCBI protein database accession number NP_079516. B7-H3 may, e.g., be obtained from RnD Systems, USA, cat. no. 1027-B3. The term "rhB7-H3" refers to recombinant human B7-H3.

A "variant" refers to an amino acid or nucleic acid sequence which differs from the parental sequence by virtue of addition (including insertions), deletion, modification and/or substitution of one or more amino acid residues or nucleobases while retaining at least one desired activity of the parent sequence disclosed herein. In the case of antibodies such desired activity may include specific antigen binding. Similarly, a variant nucleic acid sequence may be modified when compared to the parent sequence by virtue of addition, deletion and/or substitution of one or more nucleobases, but the encoded antibody retains the desired activity as described above. Variants may be naturally occurring, such as allelic or splice variants, or may be artificially constructed.

Nucleic acid hybridization reactions can be performed under conditions of different stringency. "Stringent conditions" are widely known and published in the art. Typically, during the hybridization reaction a SSC-based buffer can be used in which SSC is 0.15 M NaCl and 15 mM citrate buffer having a pH of 7.0. Increasing buffer concentrations and the presence of a denaturing agent increase the stringency of the hybridization step. For example, high stringency hybridization conditions can involve the use of (i) 50% (vol/vol) formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mcg/ml), 0.1% SDS, and 10% dextran sulfate at 42° C. with washes at 42° C. in 0.2×SSC and 0.1% SDS; (ii) 50% (vol/vol) formamide with 0.1% bovine serum albumin/0.1% ficoll/0.1% polyvinylpyrrolidone/50 mM sodium phosphate buffer at pH 6.5 with 750 mM sodium chloride, 75 mM sodium citrate at 42° C., or (iii) 10% dextran sulfate, 2×SSC, and 50% formamide at 55° C., followed by a high-stringency wash consisting of 0.1×SSC containing EDTA at 55° C. Additionally or alternatively, one, two or more washing steps using wash solutions of low ionic strength and high temperature can be included in the hybridization protocol using, for example, 0.015 M sodium chloride/0.0015 M sodium citrate/0.1% sodium dodecyl sulfate at 50° C.

The scope and meaning of any use of a term will be apparent from the specific context in which the term is used. Certain further definitions for selected terms used throughout this document are given in the appropriate context of the detailed description, as applicable.

The terms "comprising", "including," containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon—or different Likewise reference to a "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

Any embodiments specifically and explicitly recited herein may form the basis of a disclaimer either alone or in combination with one or more further embodiments.

Unless defined otherwise, all technical and scientific terms used herein have the same meaning as commonly understood to one of ordinary skill in the art to which the inventions described herein belong. All publications and patents mentioned herein are incorporated herein by reference in their entirety for the purpose of describing and disclosing, for example, the constructs and methodologies that are described in the publications, which might be used in connection with the presently described inventions.

Various aspects of the disclosure are described in further detail in the following subsections. It is understood that the various embodiments, preferences and ranges may be combined at will. Further, depending of the specific embodiment, selected definitions, embodiments or ranges may not apply.

Binding Member Characterization

The binding members provided herein specifically bind PD-L1. The binding specificity of the binding member may be verified using techniques well known in the art. In some embodiments, the PD-L1 is human PD-L1.

Binding of the binding member to PD-L1 blocks the interaction of PD-L1 with PD-1 and/or CD80, preferably with both PD-1 and CD80.

In some embodiments, the binding member provided herein is bivalent and binds hPD-L1 with a $K_D$ of lower than 10 pM as measured by KinExA®, preferably lower than 5 pM, more preferably about 3 pM, e.g., 2.9 pM, 2.8 pM or 2.7 pM. In some embodiments, such bivalent binding member is a full-length immunoglobulin. In one embodiment, said KinExA® measurements for bivalent binding members are done at room temperature. In one embodiment, the binding member is bivalent and the conditions as specified in Example 9 are used for the KinExA® measurements.

In some embodiments, the binding member provided herein is monovalent and binds hPD-L1 with a $K_D$ of lower than 50 pM as measured by KinExA®. Said $K_D$ is preferably lower than 10 pM, such as about 9 pM, e.g., 9.0 pM, 8.9 pM, 8.8 pM or 8.7 pM. In one embodiment, said KinExA® measurements for monovalent binding members are done at room temperature. In one embodiment, the binding member is monovalent and the conditions as specified in Example 4 are used for the KinExA® measurements.

In some embodiments, said monovalent binding member is a scFv. In some embodiments, said monovalent binding member is an antibody fragment having a molecular weight of about 60 kDa or lower, such as about 55 kDa, 50 kDa, 45 kDa, 40 kDa, 35 kDa, 30 kDa or 27 kDa or lower. In one embodiment, the molecular weight of the binding member is about 26 kDa, such as 23, 24, 25, 26, or 27 kDa. In particular for cancer treatment, antibody fragments may have advantages over full length antibodies when targeting the PD-1:PD-L1 signaling pathway (Maute et al (2015), PNAS, November 24; 112(47): E6506-E6514). Due to their smaller size, antibody fragments are believed to penetrate deeper into tumors than is the case with full-length antibodies, which typically have a molecular weight of about 150 kDa, or any other antibody format having a similar molecular weight or higher. Another drawback associated with full-length antibodies, in particular IgGs, is their ability to mediate cytotoxic immune responses through their Fc region (e.g., ADCC/ADCP or CDC). This inhibition may be undesirable when targeting the PD-1:PD-L1 axis as both proteins are expressed on the surface of antitumor cytotoxic T cells. Hence, administering full-length monoclonal antibodies with functional Fc parts may result in the depletion of the very lymphocytes they are intended to activate. Treatment with anti-PD-1 antibodies was found to correlate with lower circulating T-cell numbers in patients. Therefore, antibody fragments having a small molecular weight (e.g., 60 kDa or lower, such as about 55 kDa, 50 kDa, 45 kDa, 40 kDa, 35 kDa, 30 kDa or 27 kDa or lower) may offer a more effective alternative to full-length antibody therapeutics in the treatment of cancer. Thus, in preferred embodiments, the binding member is an antibody fragment selected from the group consisting of Fab, Fab', scFab, scFv, Fv fragment, nanobody, VHH, dAb, minimal recognition unit, diabody, single-chain diabody (scDb), BiTE or DART. Said formats have a molecular weight below 60 kDa and do not comprise a Fc domain.

The size and/or architecture of the binding member has implications on its half-life. To decrease side-effects in a therapeutic setting, it may be advantageous to use binding members with a short half-life. This may e.g. be achieved by using a binding member lacking an Fc part or having a modified Fc part.

In certain applications it may be advantageous to induce cytotoxic immune responses and/or activate complement and therefore, presence of a Fc domain may be desired. Thus, in one embodiment, the binding member comprises an Fc domain which is capable of mediating cytotoxic immune responses. Non-limiting examples of binding members including an Fc domain are full-length immunoglobulins, DVD-Ig, scFv-Fc and scFv-Fc.scFv fusions, IgG-scFab, scFab-dsscFv, Fv2-Fc, IgG-scFv fusions (such as e.g., bsAb, Bs1Ab, Bs2Ab, Bs3Ab, Ts1Ab, Ts2Ab, Knob-into-Holes (KiHs)), DuoBody, CrossMab.

In one embodiment, the binding member comprises an Fc domain and/or hinge which is modified such that it does not induce cytotoxic immune responses and/or or does not activate complement. Such inactivated Fc domain and/or hinge can be created by introducing one or more substitutions as thought in the art. Such binding member has the advantage of increased half-life when compared to antibody fragments having a molecular weight below 60 kDa, without mediating mediate cytotoxic immune responses.

In one embodiment, the binding member derivative lacks an Fc domain. Exemplary binding member lacking an Fc domain are Fab, Fab', scFab, scFv, Fv fragment, nanobody, VHH, minimal recognition unit, diabody, single-chain diabody (scDb), tandem scDb (Tandab), a linear dimeric scDb (LD-scDb), circular dimeric scDb (CD-scDb), BiTE (also called tandem di-scFv or tandem scFv), tandem tri-scFv, tri(a)body, bispecific Fab2, di-miniantibody, di-diabody, scFab-dsscFv or DART.

In one embodiment, the binding member comprises a constant region selected from the group consisting of human IgG1, IgG2, IgG3 or IgG4 isotype.

In one embodiment, the binding member comprises a constant region selected from the group consisting of murine IgG1, IgG2A, IgG2B, IgG3 isotype.

In one aspect, the invention provides a binding member against PD-L1, comprising (a) at least one of the VH CDR sequences CDR-H1, CDR-H2 or CDR-H3 as set forth in SEQ ID NOs: 6, 7 and 8, respectively, or variants thereof; and/or (b) at least one of the VL CDR sequences CDR-L1, CDR-L2 or CDR-L3 as set forth in SEQ ID NOs: 3, 4 and 5, respectively, or variants thereof. In some embodiments, the binding member includes at least CDR-L3 of SEQ ID NO: 5 and/or CDR-H3 of SEQ ID NO: 8, or variants thereof. In some embodiments, the binding member includes two CDR sequences selected from the group consisting of SEQ ID NOs: 6, 7 and 8, or variants thereof. In some embodiments, the binding member includes two CDR sequences selected from the group consisting of SEQ ID NOs: 3, 4 and 5, or variants thereof. In some embodiments, the binding member comprises all three CDRs of SEQ ID Nos: 6, 7 and 8 or variants thereof. In some embodiments, the binding member comprises all three CDRs of SEQ ID Nos: 3, 4 and 5 or variants thereof. Preferably, a binding member includes all CDRs as set forth in SEQ ID NOs: 3-8, or variants thereof.

The binding members provided herein possess a strong binding affinity for human PD-L1. For example, such binding member is capable of binding human PD-L1 with an equilibrium binding constant $K_D$ of lower than 100 pM, preferably lower than 75 pM, 50 pM, 25 pM, 15 pM, most preferably the $K_D$ is about 10 pM or lower, such as about 9 pM (e.g. 9.0 pM, 8.9 pM, 8.8 pM or 8.7 pM), 8 pM, 7 pM, 6 pM, 4 pM, 3 pM (2.9 pM, 2.8 pM or 2.7 pM) or lower. Affinities can be determined as described in the example section below or other methods available in the art. In a preferred embodiment, the affinity is determined by Kinetic Exclusion Assay (KinExA) at room temperature, more preferably under the conditions indicated in Example 4 for monovalent binding members or Example 9 for bivalent binding members.

The binding member described herein may be, essentially consist of, or include an antibody (such as full-length immunoglobulin) or an antibody fragment (such as a Fab, Fab', F(ab')2, scFab, scFv, Fv fragment, nanobody, VHH or minimal recognition unit) or a non-antibody scaffold. Some binding members include one or more copies of variable light and/or heavy chains as disclosed herein, e.g., a format selected from the group consisting of tandem scFvs, diabodies or a single chain diabodies (scDb), tandem scDb, linear dimeric scDb, circular dimeric scDb, a BiTE; a tandem tri-scFv, a tri(a)body, bispecific Fab2, di-miniantibody, IgGs, triabody, tetrabody, scFv-Fc-scFv fusion, di-diabody, DVD-1g, IgG-scFab, scFab-dsscFv, Fv2-Fc, or a IgG-scFv fusion (including, without being limited to, Bs1Ab, Bs2Ab, Bs3Ab, Bs4Ab, Ts1Ab and Ts2Ab), quadroma, knob-into-hole (KIH), bispecific antibodies, CrossMabs and DuoBodies.

In some embodiments, the binding member and in particular the monovalent antibody fragment above is a scFv. The VH and VL domains can be connected in either orientation, VL-linker-VH or VH-linker-VL, by a flexible linker. In a preferred embodiment, the orientation is VL-linker-VH, i.e. the light chain variable region being at the N-terminal end and the heavy chain variable region being at the C-terminal end of the polypeptide.

The binding member is preferably a humanized binding member, such as a humanized antibody, in particular a humanized antibody fragment, such as an scFv. The binding member can be monoclonal and/or chimeric.

Thus, in some embodiments, the binding member includes a variable heavy chain region of subtype VH3 and/or a variable light chain region of subtype Vkappa1.

In a preferred embodiment, the binding member comprises the VH sequence of SEQ ID NO: 2 or a variant thereof. Such variant has at least 85%, more preferably at least 90%, 91%, 92%, 93%, 94%, 95%, 96%, 97%, 98%, 99% or most preferably 100% sequence identity to SEQ ID NO: 2. Differently put, in one embodiment, the binding member comprises a VH sequence having at least 85%, more preferably at least 90%, 91%, 92%, 93%, 94%, 95%, 96%, 97%, 98%, 99% or most preferably 100% sequence identity to SEQ ID NO: 2.

Additionally or alternatively, the binding member disclosed herein comprises the VL sequence of SEQ ID NO: 1, or a variant thereof. Such variant has at least 85%, more preferably at least 90%, 91%, 92%, 93%, 94%, 95%, 96%, 97%, 98%, 99% or most preferably 100% sequence identity to SEQ ID NO: 1. Differently put, in one embodiment, the binding member comprises a VL sequence having at least 85%, more preferably at least 90%, 91%, 92%, 93%, 94%, 95%, 96%, 97%, 98%, 99% or most preferably 100% sequence identity to SEQ ID NO: 1.

In one embodiment, such binding member comprises a VH sequence having at least 85%, more preferably at least 90%, 91%, 92%, 93%, 94%, 95%, 96%, 97%, 98%, 99% or most preferably 100% sequence similarity to SEQ ID NO: 2. Additionally or alternatively, the binding member comprises a VL sequence having at least 85%, more preferably at least 90%, 91%, 92%, 93%, 94%, 95%, 96%, 97%, 98%, 99% or most preferably 100% sequence similarity to SEQ ID NO: 1.

In a much preferred embodiment, the binding member comprises the VL as set forth in to SEQ ID NO: 1 and the VH as set forth in SEQ ID NO: 2. The framework sequences of both SEQ ID NO: 1 and SEQ ID NO: 2 are derived from a human immunoglobulin described in WO 03/097697 A (ESBATech AG). Its VH and VL framework sequences have been modified for humanization and stabilization of rabbit antibodies, see, e.g., WO 2009/155726 A (ESBATech, AN ALCON BIOMEDICAL RESEARCH UNIT LLC); Borras, L., et al., JBC 2010, vol. 285(12), p. 9054.

In some embodiments, the binding member comprises one or more, preferably all VL framework sequences selected from the group consisting of SEQ ID Nos: 12 to 15.

In some embodiments, the binding member comprises one or more, preferably all VH framework sequences selected from the group consisting of SEQ ID Nos: 16 to 19.

The binding member, for example in the case of a scFv or a bispecific molecule such as a tandem scFv, a diabody or a single chain diabody, may comprise a linker sequence. In the case of a scFv, such linker sequence typically has ten to about 25 amino acids. Usually, a linker peptide is rich in glycines, which confer flexibility, as well as serines and/or threonines for improved solubility. In a preferred embodiment, a $(GGGGS)_4$ linker (SEQ ID NO: 10) or a variant thereof is used. Variations of said motif having two to five repeats may also be used. Further suitable linkers are described, e.g., in Alfthan, K., Protein Eng 1995, vol. 8(7), p. 725.

Thus, in one embodiment, such binding member comprises, has, essentially consists of or consists of an amino acid sequence that includes SEQ ID NO. 9. In some embodiments, the binding member comprises, has, essentially consists of or consists of an amino acid sequence that includes SEQ ID NO. 11.

In certain embodiments variants of the binding member provided herein are contemplated. For example, it may be desirable to improve antigen binding, antibody-dependent cell-mediated cytotoxicity (ADCC), complement-dependent cytotoxicity (CDC), to reduce susceptibility to proteolysis and/or susceptibility to oxidation, to increase stability or solubility, to decrease immunogenicity and/or to alter other biological, biochemical or biophysical properties of the binding member. In some embodiments, the variant does not show any improvement over the parent binding member. A variant may in some embodiments be a proteinaceous molecule that differs from a given binding member, in one, two, three, four, five or more positions of its amino acid sequence. Such difference may e.g., be a substitution, addition, modification or deletion.

Variants of the binding members provided herein may be prepared by protein and/or chemical engineering, introducing appropriate modifications into the nucleic acid sequence encoding the binding member, or by protein/peptide synthesis. Any combination(s) of deletions, substitutions, additions, modifications and insertions can be made to the framework or to the CDRs, provided that the generated binding member possesses the desired characteristics for which it can be screened using appropriate methods. Of particular interest are substitutions, preferably conservative substitutions as described above.

The binding member described herein may comprise one or more, such as two, three, four, five, six, seven, eight, nine, ten, eleven, twelve or more of such conservative substitutions.

Non-conservative substitutions may lead to more substantial changes, e.g., with respect to the charge, dipole moment, size, hydrophilicity, hydrophobicity or conformation of the polypeptide. In one embodiment, the binding member comprises one or more, such as two, three, four, five, six, seven, eight, nine, ten, eleven, twelve or more of such non-conservative substitutions.

Modifications may be present in the CDRs and/or in the framework sequences. For example, the CDRs provided herein may comprise one, two, three, four, five or even more modifications. For example, the CDR-L1, CDR-L2 and CDR-L3 sequences taken as a whole are at least 75%, preferably at least 76%, 77%, 78%, 79%, 80%, 85%, 90%, 91%, 92%, 93%, 94%, 95%, 96%, 97%, 98% or more preferably 99% identical to the CDRs provided herein, in particular to SEQ ID NOs: 3, 4, and 5. Additionally or alternatively, the CDR-H1, CDR-H2 and CDR-H3 sequences taken as a whole are at least 80%, preferably at least 81%, 82%, 83%, 84%, 95%, 90%, 91%, 92%, 93%, 94%, 95%, 96%, 97%, 98% or more preferably 99% identical to the CDRs provided herein, in particular to SEQ ID NOs: 6, 7 and 8.

In one embodiment the CDR-L1, CDR-L2, CDR-L3, CDR-H1, CDR-H2 and CDR-H3 taken as a whole are at least 85%, preferably at least 90%, 91%, 92%, 93%, 94%, 95%, 96%, 97%, 98% or more preferably 99% similar to the CDRs provided herein, in particular to SEQ ID NOs: 3, 4 and 5. Additionally or alternatively, the CDR-L1, CDR-L2, CDR-L3, CDR-H1, CDR-H2 and CDR-H3 taken as a whole are at least 85%, preferably at least 90%, 91%, 92%, 93%, 94%, 95%, 96%, 97%, 98% or more preferably 99% similar to the CDRs provided herein, in particular to SEQ ID NOs: 6, 7 and 8.

In one embodiment, a variant comprises one, two, three, or four substitutions in any one of sequence SEQ ID NOs: 1 to 19. In one embodiment, a variant comprises five, six, seven, eight, nine, ten, eleven or twelve substitutions in any one of sequence SEQ ID NOs: 1, 2, 9 or 11.

A particularly preferred type of variant is one where one or more entire CDRs are replaced. Typically, the CDR-H3 and CDR-L3 contribute most significantly to antigen binding. For example, the entire CDR-L1, CDR-L2, CDR-H1 and/or CDR-H2 may be replaced by a different CDR of natural or artificial origin. In some embodiments, one or more CDRs are replaced by an alanine-cassette.

Additionally or alternatively, the VH of the antibody comprises solubility enhancing point mutations. WO2009/155725 (ESBATech, a Novartis Company) describes a motif, which has proven to increase the overall solubility of the antibody. The residues are placed at positions located in the interface of the variable domain and the constant domain of an antibody and stabilize in particular antibody fragments such as scFv, lacking the constant domain. In some embodiments, in a variant of the binding member as disclosed herein one, two or all three of the following residues are present:

(i) serine (S) at heavy chain amino acid position 12 (according to AHo numbering);
(ii) serine (S) or threonine (T) at heavy chain amino acid position 103 (according to AHo numbering); and/or
(iii) serine (S) or threonine (T) at heavy chain amino acid position 144 (according to AHo numbering). In a preferred embodiment, such variant has a serine at VH position 12; a serine at VH position 103; and a threonine at VH position 144 (all AHo numbering).

Additionally or alternatively, variants may include one or more point mutations as claimed in EP2158315B1, incorporated herein by reference.

Variants may e.g. include modifications as described in WO2014/206561, incorporated herein by reference, in particular including VL framework sequences SEQ ID NOs. 15 to 22 of WO2014/206561.

Preferably, a variant binding member as described herein
(i) retains specific binding to PD-L1, in particular to hPD-L1; and/or
(ii) has a $K_D$ to human PD-L1 of lower than 100 pM, preferably lower than 75 pM, 50 pM, 40 pM, 30 pM, 20 pM, more preferably of lower than 10 pM as measured by KinExA® (the measurement preferably being made using the conditions described in Example 4 for monovalent binding members or Example 9 for bivalent binding members); and/or
(iii) is not cross-reactive with mouse PD-L1 and/or;
(iv) is cross-reactive to monkey PD-L1; and/or
(v) competes with the binding member disclosed herein for binding to PD-L1; and/or
(vi) has at least 80%, preferably at least 85%, 90%, 95% or 97% sequence identity to the sequences disclosed herein.

Variants may also be prepared by chain shuffling of light and heavy chains. A single light chain can be combined with a library of heavy chains to yield a library of variants. In one embodiment, said single light chain is selected from the group of VL sequences recited above and/or said library of heavy chains comprises one or more of the VH sequences recited above. Likewise, a single heavy chain can be combined with a library of light chains. Preferably, said single heavy chain is selected from the group of VH sequences recited above and/or said library of light chains comprises one or more of the VL sequences recited above.

A binding member can comprise any of the VL and/or the VH sequences mentioned above. Binding members having a single domain format, such as a nanobody or a VHH, comprise only one of either the VL or VH sequences mentioned above, preferably the VH sequence. Multivalent binding members, in particular F(ab')2 fragments, bis-scFv (also known as tandem scFv), diabodies, scDb, triabodies or tetrabodies and the like, preferably bispecific binding members, may comprise one or more of the VL sequences mentioned above and/or one or more of the VH sequences mentioned above.

The binding members of the instant invention, preferably the monovalent antibody fragments, more preferably the scFvs, are particularly stable. As used herein the term "stability" refers to the biophysical property of the polypeptide to remain monomeric in solution after prolonged incubation and/or incubation at elevated temperature. Unstable polypeptides tend to dimerize or oligomerize and even precipitate, thereby decreasing shelf-life and becoming less suitable for pharmaceutical applications.

The binding members provided herein and in particular the monovalent antibody fragment above remain monomeric at least to 85%, preferably at least to 90%, 91%, 92%, 93%, 94%, and most preferably to 95% after being incubated at a concentration of 10 mg/ml in PBS at pH 7.2 for 2 weeks at a temperature of 4° C., additionally or alternatively also when incubated under the same conditions at 22° C. or 37° C. In some embodiments, the binding member and in particular the monovalent antibody fragment above remains monomeric at least to 85%, preferably at least to 90%, 91%, 92%, 93%, 94%, 95%, 96% and most preferably to 97% after being incubated at a concentration of 10 mg/ml in PBS at pH 7.2 for 3 weeks at a temperature of 4° C., additionally or alternatively also when incubated under the same conditions at 22° C. or 37° C.

In some embodiments, the binding member is a scFv and forms less than 3% of dimers after 1 week or after 2 weeks of storage at 37° C. at a concentration of 10 mg/ml in PBS at pH 7.2.

The degree of monomers can, e.g., be determined by SE-HPLC (Size Exclusion HighPerformance Liquid Chromatography). A suitable mobile phase for such testing is, e.g., PBS at pH 7.2. The monomer content can be quantified by peak integration of the UV280 signal measured during the protein chromatography. A suitable system is, e.g., a Dionex Summit HPLC controlled by Chromeleon® 6.8 software that also allows for subsequent chromatogram analysis and peak quantification.

The binding member, preferably the monovalent antibody fragment above, more preferably the scFv, may have a theoretical isoelectric point (pI) in the range of 4 to 10, preferably 4 to 9, most preferably about 7.6. The theoretical pI can, for example, be calculated by using the ProtParam tool on the ExPASy Server (available at http://web.expasy-.org/protparam/; see also GASTEIGER E. et al. Protein Identification and Analysis Tools on the ExPASy Server. (In) The Proteomics Protocols Handbook. Edited by Walker J. M. Totowa: Humana Press Inc., 2005. ISBN 9781588295934. p. 571-607).

The binding member can be cross-reactive with PD-L1 from non-human species which has advantages for testing the binding member in animal models. Preferably, the binding member is cross-reactive with monkey PD-L1. In some embodiments, the KD of a monovalent binding member at room temperature in scFv format to monkey PD-L1 is about 3.3 pM as measured by KinExA®, e.g. measured under the conditions indicated in Example 5. In some embodiments, the affinity of the binding member is at least as strong, more preferably at least twice as strong for monkey PD-L1 as for human PD-L1. In some embodiments, the binding member is not cross-reactive to mouse PD-L1. Often, antibodies against a given human target have lower affinities to rodent orthologs which renders rodent in vivo animal data less valuable. As the binding members disclosed herein have comparable KD values for human and monkey PD-L1, in vivo animal data are expected to be more reflective of the disease in humans. Additionally, cross reactivity to monkey enables the use of monkey as a toxicology species.

In preferred embodiments, the binding member is not cross-reactive with other members of the B7 family, such as PD-L2 and/or B7-H3. Both proteins have high sequence similarity to PD-L1 and therefore, binding to these B7 family members would raise safety concerns.

Thus, in some embodiments, a binding member specifically binding to PD-L1 is provided, comprising at least one variable light chain of SEQ ID NO: 1 and at least one variable heavy chain of SEQ ID NO: 2, wherein said binding member has an equilibrium binding constant $K_D$ to human PD-L1 of lower than 10 pM. Preferably, said binding member remains monomeric to at least 95% in a scFv format after incubation for 1 week or 2 weeks at 37° C. in PBS at a concentration of 10 mg/ml. More preferably, said binding member is not cross-reactive to mouse PD-L1.

The invention also provides a binding member competing with the binding members disclosed herein for binding to human PD-L1. For example, such competing (or cross-blocking) binding member may be neutralizing. Preferably, such competing binding member has an equilibrium binding constant ($K_D$) for binding to human PD-L1 of 250 pM or lower, such as lower than about 100 pM, 40 pM, 30 pM, 20 pM 10 pM or lower than about 5 pM. Thus, in one embodiment, the binding member has a $K_D$ of less than about 5 pM.

As used herein, the term "competing" refers to the competition between binding members for binding to the same target. Competition can be determined by competitive binding assays in which the binding member of interest prevents or inhibits or reduces specific binding of the binding members disclosed herein to a common antigen (here, PD-L1 or a fragment thereof, respectively). Such competitive binding assays are known in the art and include, without being limited to, solid phase direct or indirect radioimmunoassay (RIA) and solid phase direct or indirect enzyme immunoassay (ELISA). Typically, such assay involves the use of purified antigen bound to a solid surface, a binding member to be tested and the reference binding member as described herein. Competitive inhibition is measured by determining the amount of either (i) the reference binding member bound to the solid surface in the presence of the binding member to be tested, or (ii) the binding member to be tested bound to the solid surface in the presence of the reference binding member. A competing binding member may bind (i) to the same epitope as the reference binding member, (ii) to an overlapping epitope, or (iii) to a different epitope on the same target molecule but sterically hindering binding of the reference binding member to its target.

Usually, when a competing binding member is present in excess, it will reduce specific binding of the binding member as described herein to PD-L1, i.e. it cross-blocks binding, by at least 40-45%, 45-50%, 50-55%, 55-60%, 60-65%, 65-70%, 70-75% or 75% or more. Preferably, binding of the binding members described herein in presence of the competing binding member is reduced by at least 80-85%, 85-90%, 90-95%, 95-97%, or 97% or more.

In one embodiment, the binding member is monovalent, such as a scFv or a Fab fragment. In another embodiment, the binding member is multivalent. Such multivalent molecule can be bivalent (such as a full-length antibody or a F(ab')2 fragment) or comprises at least three target binding sites. The multivalent binding member can be a bispecific antibody such as, e.g. a diabody, a single-chain diabody, a bis-scFv or a DART (see, e.g. Kontermann R. E. Methods in Mol. Biol. Edited by LO, B. Totowa, N.J.: Humana Press, 2004. ISBN 1588290921. p. 227). Said bispecific antibodies may well use shorter linkers then those described above for scFv, i.e., having only one to three repeats of the basic motif of SEQ ID No.: 10 (see, e.g., Holliger, P., et al., *PNAS,* 1993, vol. 90(14), p. 6444). In another embodiment, the multivalent binding member is a triabody, a minibody or tetrabody. Other examples of multivalent binding members include, without being limited to, single-chain diabodies, tandem scDb, linear dimeric scDb, circular dimeric scDb, BiTEs, tandem tri-scFv, a tri(a)bodies, bispecific Fab2, di-miniantibodies, scFv-Fc-scFv fusions, di-diabodies, DVD-Igs, IgG-scFab, scFab-dsscFv, Fv2-Fcs, or IgG-scFv fusions (including, without being limited to, Bs1Ab, Bs2Ab, Bs3Ab, Bs4Ab, Ts1Ab and Ts2Ab, quadroma, knob-into-hole (KIH), bispecific antibodies, CrossMabs and DuoBodies).

A binding member according to the present disclosure may in some embodiments include a capture moiety such as a streptavidin binding tag, e.g. the STREP-TAGS® described in US patent application US 2003/0083474, U.S. Pat. No. 5,506,121 or 6,103,493. Further examples of a capture moiety include, but are not limited to, maltose-binding protein, glutathione-S-transferase (GST), calmodulin binding peptide (CBP), FLAG-peptide (e.g. of the sequence Asp-Tyr-Lys-Asp-Asp-Asp-Asp-Lys-Gly), the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the Vesicular Stomatitis Virus Glycoprotein (VSV-G) epitope of the sequence Tyr-Thr-Asp-Ile-Glu-Met-Asn-Arg-Leu-Gly-Lys, the hemagglutinin (HA) epitope of the sequence Tyr-Pro-Tyr-Asp-Val-Pro-Asp-Tyr-Ala and the "myc" epitope of the transcription factor c-myc of the sequence Glu-Gln-Lys-Leu-Ile-Ser-Glu-Glu-Asp-Leu.

A further example of a capture moiety is a metal chelator, which is capable of binding a metal ion. A respective capture moiety may be ethylenediamine, ethylenediaminetetraacetic acid (EDTA), ethylene glycol tetraacetic acid (EGTA), diethylenetriaminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimercapto-1-propanol (-dimmercaprol), porphine or heme. In line with the standard method of immobilised metal affinity chromatography used in the art, for example an oligohistidine tag is capable of forming a complex with copper ($Cu^{2+}$), nickel ($Ni^{2+}$), cobalt ($Co^{2+}$), or zink ($Zn^{2+}$) ions, which can for instance be presented for chromatography purposes by means of the chelator nitrilotriacetic acid (NTA).

In some embodiments, the binding member disclosed herein is less immunogenic than a known binding member against PD-L1. In some embodiments, the binding member disclosed herein binds to a different epitope than a known binding member against PD-L1. In some embodiments, the binding member disclosed herein has a different clearance rate than a known binding member against PD-L1. In some embodiments, the binding member disclosed herein has an increased resistance towards aggregations and/or protease degradation than a known binding member against PD-L1. In some embodiments, the binding member disclosed herein has an improved $IC_{50}$ and/or $EC_{50}$ than a known binding member against PD-L1. In some embodiments, the binding member disclosed herein has improved binding parameters such as $k_{on}$, $k_{off}$ or $K_D$ than a known binding member to PD-L1. In some embodiments, the binding member disclosed herein has a different species cross-reactivity pattern than a known binding member against PD-L1. In some embodiments, the binding member has a different pH stability than a known binding member against PD-L1. In some embodiments, the binding member has a different long term stability at indicated temperatures than a known binding member against PD-L1. In some embodiments, the binding member shows a different tissue penetration capability than a known binding member against PD-L1. In some embodiments, the binding member has a different blocking efficacy of PD-L1 interactions with its receptors PD-1 and/or CD80 than a known binding member against PD-L1.

Also contemplated are binding members competing with the binding members disclosed herein for binding to PD-L1.

Nucleic Acids, Vectors, Host Cells and Method of Production

A binding member as described herein may be encoded by a single nucleic acid sequence or by a plurality of nucleic acid sequences. In the case of a plurality of nucleic acid sequences each sequence may encode one variable region. In some embodiments, a nucleic acid sequence may encode two or more variable regions. Generally, a plurality of nucleic acid sequences encodes the variable regions of a binding member. Typically, each variable region is encoded by one distinct nucleic acid sequence. The respective nucleic acid sequences encoding the variable regions may be included in a single nucleic acid molecule. In some embodiments two or more nucleic acid sequences encoding the variable regions are included in a single nucleic acid molecule. In some embodiments, each nucleic acid sequence encoding a variable region is included in a single distinct nucleic acid molecule. Accordingly, a plurality of nucleic acid molecules may be used in the production of a binding member, for example each encoding at least one variable region. A respective nucleic acid molecule may in some embodiments define an expression cassette. As indicated above, an expression cassette is a nucleic acid molecule capable of directing expression of a particular nucleotide sequence in an appropriate host cell.

An expression cassette includes a promoter operatively linked to the nucleotide sequence of interest, which is operatively linked to one or more termination signals. It may also include sequences required for proper translation of the nucleotide sequence. The coding region can encode a polypeptide of interest and can also encode a functional RNA of interest, including but not limited to, antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, however, the expression cassette is heterologous with respect to the host; i.e., the particular nucleic acid sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant or an animal, the promoter can also be specific to a particular tissue, organ, or stage of development.

Knowing the sequence of the binding member or of its parts, cDNAs encoding the polypeptide sequence can be generated by methods well known in the art, e.g. by gene synthesis. These cDNAs can be cloned by standard cloning and mutagenesis techniques into a suitable vector such as an expression vector or a cloning vector. Optionally, the variable light chain is encoded by a separate vector than the variable heavy chain of the antibody. Further, additional sequences such as a tag (e.g., a His-tag), a constant domain for the production of a Fab or a full-length antibody, a linker, the coding sequence of a second binding specificity or another functional polypeptide such as an enzyme to generate a fusion construct or a bispecific molecule may be included into the genetic construct.

Based on the cloning strategy chosen, genetic constructs may generate a binding member having one or more additional residues at the N-terminal or C-terminal end. For example, an N-terminal methionine derived from the start codon or an additional alanine may be present in an expressed polypeptide, unless it has been clipped off post-translationally. It is therefore to be understood that the antibodies disclosed herein comprise the disclosed sequences rather than consist of them. Thus, in one embodiment, the binding member comprises the sequence of SEQ ID NO: 9. In another embodiment, the binding member comprises the sequence of SEQ ID NO: 11. If the binding member is a scFv having the orientation VH-linker-VL or any other antibody fragment where the VH is placed N-terminally, the VH sequence part of the molecule may be N-terminally methylated. Thus, in one embodiment, SEQ ID NO: 2 has an N-terminal methionine.

Basic protocols of standard cloning, mutagenesis and molecular biology techniques are described in, e.g., Molecular Cloning, A Laboratory Manual (Green M. and Sambrook, J. Molecular Cloning: a Laboratory Manual. 4th edition. Cold Spring Harbor Laboratory, 2012. ISBN 1936113422.).

Further contemplated are isolated nucleic acids hybridizing with the nucleic acids described herein under stringent conditions.

Also contemplated are cells recombinantly expressing the binding members disclosed herein. Appropriate host cells for the expression of the genetic constructs can be prokaryotic or eukaryotic. Suitable prokaryotic host cells are gram-negative or gram-positive and include species of the *Escherichia, Ervinia, Enterobacter, Klebsiella, Pseudomonas* or *Bacillus* families. In some embodiments, the host cell is *Escherichia coli*, such as one or more of *E. coli* strains BL21 (DE3) (for example Invitrogen, USA, cat. no. C600003) and Origami™ 2(DE3) (for example Novagen, USA, cat. no. 71345-3).

If post-translational modifications such as glycosylation or phosphorylation are desired, it may be advantageous to use a eukaryotic host cell. For example, eukaryotic microbes such as commonly used *Saccharomyces cerevisiae* or *Pichia pastoris* strains may serve as a host cell. Suitable examples of a host cells also include a plant or an animal cell, in particular insect or mammalian cells. Suitable mammalian cells include, without being limited to, Chinese Hamster Ovary Cells (CHO), Human Embryonic Kidney Cells (HEK), Human Umbilical Vein Endothelial Cells (HUVEC) or NS0 myeloma cells. Glycosylation in prokaryotic host cells as also been reported, see e.g. Jaffe S. R. P. et al., Curr. Opin. Biotechnol. 2014, vol. 30, p. 205.

The binding member can be produced by way of expression in a suitable host cell. For example, the expression vectors described above are introduced into a host cell by standard techniques such as electroporation or chemical transformation. The transformed cells are then cultivated under conditions adequate for recombinant protein expression, typically in appropriate nutritional media, optionally modified for inducing promotors, selecting transformants, or amplifying encoding sequences of interest. The binding member is recovered from the culture and optionally purified using standard techniques in the art. The yield of recombinant protein may be improved by optimizing media and culture conditions such as temperature or oxygen supply. In prokaryotes, the binding member can be produced in the periplasm, intracellularly as inclusion bodies or be secreted into the medium. Animal cells will typically secrete the binding member into the medium. Upon harvest, the protein can be purified using methods well known in the art such as gel filtration, ion exchange chromatography, reversed phase chromatography, hydrophobic interaction, mixed mode chromatography and/or affinity chromatography.

In one embodiment, the binding member is produced in a cell-free system. This typically involves in vitro transcription followed by in vitro translation of nucleic acid product templates encoding a protein as described herein, e.g., plasmid DNA or PCR product templates. For example, crude lysates from growing cells are used, providing the necessary enzymes as well as the cellular protein synthesis machinery. The necessary building blocks such as amino acids or nucleobases as well as energy delivering molecules and others can be exogenously supplied. Cell-free expression systems can, for example, be based on lysed rabbit reticulocytes (e.g., Rabbit Reticulocyte Lysate System, Promega, cat. no. L4540), HeLa cells (e.g., 1-Step Human In Vitro Translation Kit, 88881, Thermo Scientific), insect cells (e.g., EasyXpress Insect Kit II, 32561, Qiagen), wheat germs (e.g., Wheat Germ Extract, L4380, Promega), or *E. coli* cells (e.g., PURExpress® In Vitro Protein Synthesis Kit, E6800S, NEB). Also, optimized cell-free antibody expression systems for improved disulfide bond generation can be used for production. Commercially available kits include insect cell lysates (e.g., EasyXpress Disulfide Insect Kit, 32582, Qiagen) or *E. coli* cell lysates (e.g., EasyXpress Disulfide *E. coli* Kit, 32572, Qiagen). Cell-free protein synthesis has, e.g., the advantage of being fast, achieving high product yields, allowing for easy modification of reaction conditions, forming a low degree of or even no byproducts. Cell-free protein synthesis may involve biological and/or chemical steps which cannot be conducted in purely biological or chemical production systems. For example, non-natural or chemically-modified amino acids can be incorporated into the protein at desired positions. ScFv-toxin fusion proteins have been successfully produced in cell-free systems (Nicholls, P. J., et al., *JBC* 1993, vol. 268, pp. 5302-5308). Thus, in one embodiment a method of producing the binding member described herein is provided, which includes the steps of (a) providing a cell-free system, (b) providing a nucleic acid product template encoding the binding member above, (c) allowing for transcription and translation of the nucleic acid product template; (d) recovering; and optionally (e) purifying the binding member, respectively.

Additionally or alternatively, a method of producing the binding member described herein includes at least one step of chemical synthesis. For example, the method may be entirely chemical. In another embodiment, the cell-based or the cell-free production systems described above include such at least one step of chemical synthesis.

In some embodiments, a binding member as described herein is produced in a cell-based system using an expression vector for intracellular expression in *E. coli*. Upon expression, the polypeptide is generated as an inclusion body within the host cell which is separated from further cell particles followed by solubilisation in a denaturing agent such as guanidine hydrochloride (GndHCl) and refolded by renaturation procedures well known to the skilled person.

The desired binding member may also be produced in a transgenic animal. A suitable transgenic animal may be obtained according to standard methods, for example including the steps of (i) making the transgenic embryo, e.g. by micro injecting DNA constructs that include the coding sequence of the binding members as well as suitable control sequences into eggs; (ii) transferring the eggs into pseudo-pregnant recipient females; (iii) monitoring gestation or pregnancy; and (iv) selecting a descendant expressing the desired antibody.

It is to be understood that the nucleic acids, vectors, host cells and method of production described above also apply to the binding members (insofar as they are a protein) described herein.

Further contemplated herein are cells expressing chimeric antigen receptors (CARs). CAR expressing cells have found ample use in cancer treatment. Such cells, either of autologous or allogeneic origin, are genetically modified to express CARs, e.g. by traducing the cells with lentiviral vectors. Cells are commonly T cells, whereas NK cells have also found use. A CAR typically has several sections, comprising an antigen binding domain, a spacer, a transmembrane domain, a costimulatory signaling domain, and a signaling domain.

The extracellular antigen-binding domain specifically recognizes a given target protein, usually on a cancer cell. Upon binding to the target, the CAR cell is activated and also kept in proximity to the cancer cell. The antigen-binding domain is connected via a spacer to a transmembrane domain which in turn is connected to the intracellular costimulatory signaling domain. The length of the spacer may have to be optimized, depending on the characteristics of the antigen-binding domain and its target protein. Binding of the target to the cancer cell triggers as conformational change that leads to an activation signal by the signaling domain, e.g., a CD3 zeta signaling domain. The costimulatory signaling domain, typically located between the transmembrane domain and the signaling domain, serves in amplifying the activation signal. Exemplary embodiments of costimulatory signaling domains are CD28 or 4-1BB.

In some embodiments, the antigen binding domain comprises the VL and/or VH sequences as described herein. In some embodiments, the antigen binding domain comprises a scFv as described herein.

In some embodiments, the CAR expressing cell is an "armored CAR" cell, i.e. a CAR expressing cell which secretes soluble proteins to modify the immune response within the tumor microenvironment of the subject to which the CAR cells were administered. In some embodiments, such cell excretes a binding member as described herein, in particular a scFv.

Chemical and/or Biological Modifications

In one aspect, the binding member disclosed herein is chemically and/or biologically modified. Such modification may include, but is not limited to, glycosylation, PEGylation, HESylation, Albumin fusion technology, PASylation, labelling with dyes and/or radioisotopes, conjugation with enzymes and/or toxins, phosphorylation, hydroxylation and/or sulfation. Likewise, any binding member, the nucleic acid sequence, the vector and/or the host cell described above can be modified accordingly.

Chemical and/or biological modifications may be conducted to optimize pharmacodynamics or water solubility of the protein or to lower its side effects. For example, PEGylation, PASylation and/or HESylation may be applied to slow down renal clearance and thereby increase plasma half-life time of the binding member. Additionally or alternatively, a modification may add a different functionality to the protein, e.g. a toxin to more efficiently combat cancer cells, or a detection molecule for diagnostic purposes.

Glycosylation refers to a process that attaches carbohydrates to proteins. In biological systems, this process is performed enzymatically within the cell as a form of co-translational and/or post-translational modification. A protein, here the binding member such as an antibody, can also be chemically glycosylated. Typically, but not limited to, glycosylation is (i) N-linked to a nitrogen of asparagine or arginine side-chains; (ii) O-linked to the hydroxy oxygen of serine, threonine, tyrosine, hydroxylysine, or hydroxyproline side-chains; (iii) involves the attachment of xylose, fucose, mannose, and N-acetylglucosamine to a phosphoserine; or (iv) in form of C-mannosylation wherein a mannose sugar is added to a tryptophan residue found in a specific recognition sequence. Glycosylation patterns can, e.g., be controlled by choosing appropriate cell lines, culturing media, protein engineering manufacturing modes and process strategies (HOSSLER, P. Optimal and consistent protein glycosylation in mammalian cell culture. *Glycobiology* 2009, vol. 19, no. 9, p. 936-949.). In some embodiments, the glycosylation patterns of the binding members described herein are modified to enhance ADCC and CDC effector function.

Protein engineering to control or alter the glycosylation pattern may involve the deletion and/or the addition of one or more glycosylation sites. The creation of glycosylation sites can conveniently be accomplished by introducing the corresponding enzymatic recognition sequence into the amino acid sequence of the binding member or by adding or substituting one or more of the above enumerated amino acid residues.

It may be desirable to PEGylate the binding member. PEGylation may alter the pharmacodynamic and pharmacokinetic properties of a protein. Polyethylene-glycol (PEG) of an appropriate molecular weight is covalently attached to the protein backbone (see, e.g., Pasut G. and Veronese F. State of the art in PEGylation: the great versatility achieved after forty years of research. *J. Control Release,* 2012, vol. 161, no. 2, p. 461). PEGylation may additionally reduce the immunogenicity by shielding the PEGylated protein from the immune system and/or alter its pharmacokinetics by, e.g. increasing the in vivo stability of the binding member, protecting it from proteolytic degradation, extending its half-life time and by altering its biodistribution.

Similar effects may be achieved by PEG mimetics, e.g., HESylating or PASylating the antibody. HESylation utilizes hydroxyethyl starch ("HES") derivatives, whereas during PASylation the antibody becomes linked to conformationally disordered polypeptide sequences composed of the amino acids proline, alanine and serine. These PEG mimetics and related compounds are, e.g., described in Binder U. and Skerra, A. Half-Life Extension of Therapeutic Proteins via Genetic Fusion to Recombinant PEG Mimetics, in Therapeutic Proteins: Strategies to Modulate Their Plasma Half-Lives. Edited by Kontermann R., Weinheim, Germany: Wiley-VCH, 2012. ISBN: 9783527328499. p. 63.

The binding member may include an epitope such as a salvage receptor binding epitope. Such salvage receptor binding epitope typically refers to an epitope of the Fc region of an IgG molecule (e.g., IgG1, IgG2, IgG3, or IgG4) and has the effect of increasing the in vivo half-life of the molecule.

Additionally or alternatively, the binding member is labelled with or conjugated to a second moiety which ascribes ancillary functions following target binding. The second moiety may, e.g., have an additional immunological effector function, be effective in drug targeting or useful for detection, without being limited thereto. The second moiety can, e.g., be chemically linked or fused genetically to the binding member using known methods in the art.

Molecules which may serve as second moiety include, without being limited to, a radionuclide, also called a radioisotope, an apoenzyme, an enzyme, a co-factor, a peptide moiety such as a HIS-tag, a protein, a carbohydrate such as a mannose-6-phosphate tag, a fluorophore such as fluorescein isothiocyanate (FITC), phycoerythrin, a green/blue/red or other fluorescent protein, allophycocyanin (APC), a chromophore, a vitamin such as biotin, a chelator, an antimetabolite such as methotrexate, a liposome, a toxin such as a cytotoxic drug, or a radiotoxin. Illustrative examples of a radionuclide are $^{35}S$, $^{32}P$, $^{14}C$, $^{18}F$, and $^{125}I$. Examples of suitable enzymes include, but are not limited to, alkaline phosphatase, horseradish peroxidase, beta-galactosidase and angiogenin. An illustrative example of a suitable protein is a lectin. Examples of suitable cytotoxic drugs include, but are not limited to, taxol, gramicidin D and colchicine.

A labelled binding member is particularly useful for in vitro and in vivo detection or diagnostic purposes. For example, a binding member labelled with a suitable radioisotope, enzyme, fluorophore or chromophore can be detected by radioimmunoassay (RIA), enzyme-linked immunosorbent assay (ELISA), or flow cytometry-based single cell analysis (e.g., FACS analysis), respectively. Similarly, the nucleic acids and/or vectors disclosed herein can be used for detection or diagnostic purposes, e.g. using labelled fragments thereof as probes in hybridization assays. Labelling protocols may, e.g., be found in Johnson I. and Spence, M. T. Z. Molecular Probes Handbook, A Guide to Fluorescent Probes and Labelling Technologies. Life Technologies, 2010. ISBN: 0982927916.

Compositions

A binding member, a nucleic acid sequence and/or a vector as disclosed herein may be provided in a composition which further includes a suitable carrier, excipient or diluent. In typical embodiments, a respective composition includes an antibody described herein.

Such composition can, e.g., be a diagnostic, a cosmetic or a pharmaceutical composition. For therapeutic or cosmetic purposes, the composition is a pharmaceutical composition including a pharmaceutically acceptable carrier, excipient or diluent, i.e. not being toxic at the dosages and a concentration employed.

Suitable "carrier", "excipients" or "diluents" include, without being limited to: (i) buffers such as phosphate, citrate, or other, organic acids; (ii) antioxidants such as ascorbic acid and tocopherol; (iii) preservatives such as 3-pentanol, hexamethonium chloride, benzalkonium chloride, benzyl alcohol, alkyl paraben, catechol, or cyclohexanol; (iv) amino acids, such as e.g. histidine, arginine; (v) peptides, preferably up to 10 residues such as polylysine; (vi) proteins, such as bovine or human serum albumin; (vii) hydrophilic polymers such as polyvinylpyrrolidone; (viii) monosaccharides, disaccharides, polysaccharides and/or other carbohydrates including glucose, mannose, sucrose, mannitol, trehalose, sorbitol, aminodextran or polyamidoamines; (ix) chelating agents, e.g. EDTA; (x) salt-forming ions such as sodium, potassium and/or chloride; (xi) metal complexes (e.g. Zn-protein complexes); (xii) ionic and non-ionic surfactants such as TWEEN™, PLURONICS™ or polyethylene glycol (PEG), and/or (xiii) cryopreservatives such as dimethyl sulfoxide (DMSO).

Many of the exemplary compounds have different functions and may, e.g., act as carrier and as diluent. It is also to be understood that the composition may include more than one of each carrier, diluent or excipient.

The binding member, the nucleic acid sequences or the vector may be provided on solid support materials such as beads, microparticles or nanoparticles. Typically, a binding member molecule is linked to such carrier via a covalent bond (optionally involving a linker), a non-covalent bond or both. The beads and microparticles can include, for example, starch, cellulose, polyacrylate, polylacetate polyglycolate, poly(lactide-co-glycolide), latex, or dextran.

In one embodiment, a pharmaceutical composition is provided, which includes the binding member, the nucleic acid sequences or the vector as described above. The composition may furthermore include one or more additional therapeutically active compounds in a therapeutically effective amount. The additional therapeutically active compound is in some embodiments a compound active against an PD-L1-mediated disease.

Therapeutic Applications

A molecule as described herein, in particular the binding member (such as an antibody), the nucleic acid molecule, the host cell or the vector, is useful as a medicament. Typically, such a medicament includes a therapeutically effective amount of a molecule or cell as provided herein. Accordingly, a respective molecule or host cell can be used for the production of a medicament useful in the treatment of one or more PD-L1 related disorders.

In one aspect, a method of treating a PD-L1 related/PD-L1 mediated disorder is provided. The method includes the steps of administering a pharmaceutically effective amount of a molecule or host cell as described herein, in particular the antibody or host cell, to a subject in need thereof. In one embodiment, the pharmaceutical composition described above, which includes such pharmaceutically effective amount of the binding member, e.g. antibody, or the host cell is administered to the subject. The medicament referred to above may be administered to a subject.

The subject in need of a treatment can be a human or a non-human animal. Typically, the subject is a mammal, e.g., a mouse, a rat, rabbit, a hamster, a dog, a cat, a monkey, an ape, a goat, a sheep, a horse, a chicken, a guinea pig or a pig. In typical embodiments, the subject is diagnosed with a PD-L1-related disorder or may acquire such a disorder. In case of an animal model, the animal might be genetically engineered to develop a PD-L1 related disorder. In an animal model an animal may also be genetically engineered in such a way that it shows the characteristics of a PD-L1 mediated disease.

A variety of PD-L1 related disorders are known, in which an antagonist of PD-L1 has shown a therapeutic effect in, including, without being limited to, NSCLC (non-small cell lung carcinoma), urothelial cancer, melanoma, renal cell carcinoma, Hodgkin's lymphoma, head and neck squamous cell carcinoma, ovarian cancer, gastrointestinal cancer, hepatocellular cancer, glioma, breast cancer, lymphoma, small cell lung carcinoma, myelodysplastic syndromes, prostate cancer, bladder cancer, cervical cancer, non-clear cell kidney cancer, colorectal cancer, sarcomas, colon cancer, kidney cancer, lung cancer, pancreatic cancer or gastric cancer, skin cancer, uterine cancer, glioblastoma, leukemia, carcinoma, Merkel cell carcinoma or renal cell carcinoma (RCC), blood cancer, multiple myeloma, lymphoblastic leukemia (ALL), B cell leukemia, chronic lymphocytic leukemia, non-Hodgkin's lymphoma, and ovarian cancer; or wherein said disease is systemic lupus erythematosus.

The PD-1 pathway has also been shown to be involved in sepsis and related disorders (see, e.g. WO2015038538). Thus, in one embodiment, the PD-L1 related disease is sepsis, septic shock, systemic inflammatory response syndrome, or compensatory anti-inflammatory response syndrome.

Bodhankar et al. ((2015) Stroke 46(10): 2926-34) demonstrated beneficial therapeutic effects of treatment with an anti-PD-L1 monoclonal antibody in the middle cerebral artery occlusion mouse model of experimental stroke.

PD-1 and PDL-1 are immunohistochemically detectable in primary central nervous system lymphomas and may be involved in creating an immunosuppressive microenvironment (Berghoff et al., (2014) Clinical Neuropathology 33(1): 42-9). Specific immune checkpoint inhibitors may be considered for experimental therapy approaches in this disease.

The impact of the PD-1/PD-L1 interaction on acute leukaemia in the post-transplant setting has been evaluated in both mice and humans. Koestner et al. ((2011), Blood 117(3): 1030-1041) observed restoration of a graft-versus-lymphoma effect without triggering graft-versus-host disease by PD-L1 blockade in mouse models: the adoptive transfer of gene-modified allogeneic T cells early after transplantation of hematopoietic stem cells provided a potent graft-versus-lymphoma effect without graft-versus-host disease, whereas later adoptive transfer was effective only with concurrent PD-L1 blockade. The T cells were engineered to express T-cell receptors (TCRs) against a recipient leukaemia-specific antigen.

The pharmaceutical composition may be applied by one or more of various suitable routes of administration. Administration can for instance be conducted parenterally. In some embodiments administration is carried out intramuscularly. In some embodiments administration is carried out intravenously as a bolus or by continuous infusion. Administration is in some embodiments conducted intraarticularly, intrasynovially, subcutaneously, topically (e.g., to the skin or the eye), parenterally, rectally, intradermally, subcutaneously, transdermally, percutanously or locally. Further suitable modes of administration include, but are not limited to intracerebrally, intracerebrospinally, intrathecally, epidurally, or intraperitoneally, orally, urogenitally, intravitreally, systemically, intravenously, intraperitoneal, intramuscularly, intraocularly, oticly, intranasally, by inhalation, sublingually, intracranially, intramuscularly, intraperitoneally or buccally, for example. A binding member disclosed herein, a nucleic acid sequence, a vector or a host cell disclosed herein can be combined with one or more further therapeutically effective compounds. Such a compound may in some embodiments be capable of disrupting signalling via a PD-L1 receptor. A respective compound may in some embodiments be capable of inhibiting one or more additional targets such as, e.g., other mediators of inflammatory responses. Such compound(s) can be administered simultaneously or sequentially.

For therapeutic applications, the binding member may also be radiolabelled or linked to a toxin or linked to another effector function as described above.

Generally, therapeutic use of the binding members described herein may be in combination with one or more therapies selected from the group of antibody therapy, chemotherapy, cytokine therapy, dendritic cell therapy, gene therapy, hormone therapy, laser light therapy, radiation therapy or vaccine therapy.

In some embodiments, the binding member is administered in combination with one or more different pharmaceutical compounds. Exemplary examples include CTLA-4 inhibitors (such as tremelimumab and/or ipilimumab), VEGF inhibitors (such as bevacizumab), EGF receptor inhibitors (e.g., erlotinib), cytostatics (e.g., cisplatin, pemetrexed, carboplatin and/or paclitaxel), IFN-g, cancer vaccine, soluble CD80 or combinations thereof. An overview of clinical trials involving anti-PD-L1 antibodies in combination with one or more pharmaceutical compounds is given in He J et al (2015), Nature Scientific Reports; 5:13110; DOI: 10.1038/srep13110. Chemotherapeutic agents which may be administered in combination include, without being limited to, alkylating agents, antimetabolites, antitumor antibiotics, alkaloids, nitrosourea agents, topoisomerase inhibitors, hormone or antagonist thereof, aromatase inhibitors, P-glycoprotein inhibitors and/or a platinum complex derivative. Exemplary embodiments of chemotherapeutic agents are gemcitabine, cyclophsphamine, 5-fluoroucil, oxaliplatin, Black et al. (2016) Oncotarget 7(9):10557-67 showed in a panel of PD-L1-expressing human and mouse breast and prostate cancer cell lines that activation of the PD-1/PD-L1 immune checkpoint confers tumor cell chemoresistance associated with increased metastasis. They also showed that inhibition of the PD-1/PD-L1 axis using anti-PD-1 antibody enhanced doxorubicin chemotherapy to inhibit metastasis in a syngeneic mammary orthotopic mouse model of metastatic breast cancer. They conclude that combinations of chemotherapy and immune checkpoint blockade may limit chemoresistance and progression to metastatic disease.

In one embodiment, the antibody described herein is administered in combination with a vaccine to a subject with persistent viral infection. In murine models, it was shown that blocking PD-1/PD-L1 inhibitory signals on exhausted CD8+ T cells, in combination with therapeutic vaccination, synergistically enhances functional CD8+ T cell responses and improves viral control even in the absence of CD4(+) T cell help (see e.g., Ha S J et al, J Exp Med. 2008 Mar. 17; 205(3):543-55 and EP2079760B1). The subject may e.g. have a persistent viral infection with adenovirus, cytomegalovirus, human immondeficiency virus (HIV), Epstein-Barr virus, hepatitis virus, herpes virus, papovavirus, papillomavirus, parvovirus, T cell leukemia virus, T-lymphotrophic virus (HTLV) and/or varicella-zoster virus.

Also contemplated are methods of inhibiting growth of a tumor or a tumor cell, comprising the step of contacting the tumor or tumor cell with a therapeutically effective amount of the binding member disclosed herein. In one embodiment, the administration educes tumor growth, in another embodiment, administration decreases tumor size.

Diagnostic Applications and/or Detection Purposes

A binding member as disclosed herein may be used for detection or diagnostic purposes in vivo and/or in vitro. For example, a wide range of immunoassays involving antibodies for detecting the expression in specific cells or tissues are known to the skilled person. Likewise, any binding member, the nucleic acid sequence, the vector and/or the host cell described in the preceding text can be used accordingly as detailed in this section.

The expression status of tumoral PD-L1 has been shown to be prognostic in multiple tumor types, including, without being limited to melanoma, renal cell carcinoma, and non-small-cell lung cancer. PD-L1 expression can measured by immunohistochemistry (IHC) for which anti-PD-L1 antibodies are essential.

For such applications, the binding member (e.g. the antibody), the nucleic acid sequence, the vector or the host cell disclosed herein may include a detectable label. In some embodiments, the binding member, the nucleic acid sequence, the vector or the host cell disclosed herein does not include a detectable label. As an illustrative example, an unlabelled antibody may be used and detected by a secondary antibody specifically binding to an epitope on the binding member, e.g. antibody, described herein.

In some embodiments, the binding member, nucleic acid sequence, vector and/or host cell is coupled to one or more substances that can be recognized by a detector substance. As an example, the binding member may be covalently linked to biotin, which can be detected by means of its capability to bind to streptavidin. Likewise, the nucleic acids and/or vectors disclosed herein can be used for detection or diagnostic purposes, e.g., by using labelled fragments thereof as probes in hybridization assays.

In certain embodiments, any of the molecules provided herein, in particular the antibody, is useful for detecting the presence of PD-L1 in a sample, preferably a sample of biological origin. The term "PD-L1" as used in this context includes full-length PD-L1, fragments thereof and/or precursors thereof. The term "detecting" encompasses quantitative and/or qualitative detection. In certain embodiments, a biological sample includes a cell or tissue from human patients. Non-limiting examples of biological samples include blood, urine, cerebrospinal fluid, biopsy, lymph and/or non-blood tissues.

In certain embodiments, the method includes contacting the biological sample with a binding member to PD-L1 (such as an anti-PD-L1 antibody) as described herein under conditions permissive for binding of the inhibitor to its target PD-L1, if present, and detecting the inhibitor-target complex. Such method may be an in vitro or in vivo method. In one embodiment, such binding member is used to select subjects eligible for therapy with the binding members described herein, e.g., where PD-L1 is a biomarker for selection of patients.

In another aspect, the binding member, e.g. an antibody, is used in cosmetic applications, e.g., for improving the aesthetic appearance of skin.

Likewise, a nucleic acid sequence, a vector and/or a host cell described above can be used accordingly as detailed above.

Article of Manufacture

In a further aspect, an article of manufacture (i.e., a kit) is provided. The article of manufacture includes matter, e.g. material, useful for (i) the treatment, prevention of delay of progression of PD-L1 related disorders; for (ii) diagnostic or for (iii) cosmetic purposes. The article of manufacture may include instructions for use and one or more containers. Suitable containers include, for example, bottles, vials, syringes, cartridges, plates and test tubes and may be made from a variety of materials such as glass or plastic. At least one container holds a composition that includes a binding member as disclosed herein. The container may have a sterile access port. A respective container is typically labelled.

The reagents are typically provided in predetermined amounts of dry powders, usually lyophilized, including excipients which after dissolution will provide a reagent solution having the appropriate concentration. Other additives such as stabilizers and/or buffers may also be included. If the binding member is labelled with an enzyme, the kit will typically include the according substrates and cofactors.

The instructions for use may provide indications that the composition is used for the treatment, prevention and/or delay of progression of a disorder of choice; or instructions for performing a detection or diagnostic assay. The instructions may be provided on a label and/or on a package insert.

SEQUENCES REFERRED TO

The sequences disclosed herein are:

SEQ ID NO: 1-VL of scFv1
EIVMTQSPSTLSASVGDRVIITCQASEDIYSLLAWYQQKPGKAPKLLIYD

ASDLASGVPSRFSGSGSGAEFTLTISSLQPDDFATYYCQGNYGSSSSSSY

GAVFGQGTKLTVLG

SEQ ID NO: 2-VH of scFv1
EVQLVESGGGLVQPGGSLRLSCTVSGIDLSSYTMGWVRQAPGKGLEWVGI

ISSGGRTYYASWAKGRFTISRDTSKNTVYLQMNSLRAEDTAVYYCARGRY

TGYPYYFALWGQGTLVTVSS

SEQ ID NO: 3-CDR-L1 of scFv1
QASEDIYSLLA

SEQ ID NO: 4-CDR-L2 of scFv1
DASDLAS

SEQ ID NO: 5-CDR-L3 of scFv1
QGNYGSSSSSSYGAV

SEQ ID NO: 6-CDR-H1 of scFv1
IDLSSYTMG

SEQ ID NO: 7-H2 of scFv1
IISSGGRTYYASWAKG

SEQ ID NO: 8-H3 of scFv1
GRYTGYPYYFAL

SEQ ID NO: 9-scFv1
EIVMTQSPSTLSASVGDRVIITCQASEDIYSLLAWYQQKPGKAPKLLIYD

ASDLASGVPSRFSGSGSGAEFTLTISSLQPDDFATYYCQGNYGSSSSSSY

GAVFGQGTKLTVLGGGGGSGGGGSGGGGSGGGGSEVQLVESGGGLVQPGG

SLRLSCTVSGIDLSSYTMGWVRQAPGKGLEWVGIISSGGRTYYASWAKGR

FTISRDTSKNTVYLQMNSLRAEDTAVYYCARGRYTGYPYYFALWGQGTLV

TVSS

SEQ ID NO: 10-linker
GGGGSGGGGSGGGGSGGGGS

SEQ ID NO: 11 methylated scFv1
MEIVMTQSPSTLSASVGDRVIITCQASEDIYSLLAWYQQKPGKAPKLLIY

DASDLASGVPSRFSGSGSGAEFTLTISSLQPDDFATYYCQGNYGSSSSSS

YGAVFGQGTKLTVLGGGGGSGGGGSGGGGSGGGGSEVQLVESGGGLVQPG

GSLRLSCTVSGIDLSSYTMGWVRQAPGKGLEWVGIISSGGRTYYASWAKG

RFTISRDTSKNTVYLQMNSLRAEDTAVYYCARGRYTGYPYYFALWGQGTL

VTVSS

SEQ ID NO: 12-FR-L1
EIVMTQSPSTLSASVGDRVIITC

SEQ ID NO: 13-FR-L2
WYQQKPGKAPKLLIY

SEQ ID NO: 14-FR-L3
GVPSRFSGSGSGAEFTLTISSLQPDDFATYYC

SEQ ID NO: 15-FR-L4
FGQGTKLTVLG

SEQ ID NO: 16-FR-H1
EVQLVESGGGLVQPGGSLRLSCTVSG

SEQ ID NO: 17-FR-H2
WVRQAPGKGLEWVG

SEQ ID NO: 18-FR-H3
RFTISRDTSKNTVYLQMNSLRAEDTAVYYCAR

SEQ ID NO: 19-FR-H4
WGQGTLVTVSS

SEQ ID NO: 20-Heavy Chain of IgG_1
EVQLVESGGGLVQPGGSLRLSCTVSGIDLSSYTMGWVRQAPGKGLEWVGI

ISSGGRTYYASWAKGRFTISRDTSKNTVYLQMNSLRAEDTAVYYCARGRY

TGYPYYFALWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

SEQ ID NO: 21-Heavy Chain of IgG_2
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSAASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

SEQ ID NO: 22-Heavy Chain of IgG_3
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 23-Heavy Chain of IgG_4
EVQLVESGGGVVRPGGSLRLSCAASGFTFDDYGMTWVRQAPGRGLEWVSG

IHWHGKRTGYADSVKGRFTISRDNAKKSLYLQMNSLKGEDTALYHCVRGG

MSTGDWFDPWGQGTLVIVSSAKTTAPSVYPLAPVCGDTTGSSVTLGCLVK

GYFPEPVTLTWNSGSLSSGVHTFPAVLQSDLYTLSSSVTVTSSTWPSQSI

TCNVAHPASSTKVDKKIEPRGPTIKPCPPCKCPAPNLLGGPSVFIFPPKI

KDVLMISLSPIVTCVVVDVSEDDPDVQISWFVNNVEVHTAQTQTHREDYN

STLRVVSALPIQHQDWMSGKEFKCKVNNKDLPAPIERTISKPKGSVRAPQ

VYVLPPPEEEMTKKQVTLTCMVTDFMPEDIYVEWTNNGKTELNYKNTEPV

LDSDGSYFMYSKLRVEKKNWVERNSYSCSVVHEGLHNHHTTKSFSRTPGK

SEQ ID NO: 24-Light Chain of IgG_1
EIVMTQSPSTLSASVGDRVIITCQASEDIYSLLAWYQQKPGKAPKLLIYD

ASDLASGVPSRFSGSGSGAEFTLTISSLQPDDFATYYCQGNYGSSSSSSY

GAVFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

SEQ ID NO: 25-Light Chain of IgG_2
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 26-Light Chain of IgG_3
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO: 27-Light Chain of IgG_4
DIQMTQSPSSLSASLGDRVTITCRASQSINSYLNWYQQKPGKAPKLLIYV

ASSLQSGVPSRFSGSGSGTEFTLTISNLQPEDFATYYCQQSYSTPPITFG

QGTRLEIKRADAAPTVSIFPPSSEQLTSGGASVVCFLNNFYPKDINVKWK

IDGSERQNGVLNSWTDQDSKDSTYSMSSTLTLTKDEYERHNSYTCEATHK

TSTSPIVKSFNRNEC

The following are examples, illustrating the methods and compositions disclosed herein. It is understood that various other embodiments may be practiced, given the general description provided above.

EXAMPLES

Example 1—Identification of PD-L1 Binding scFvs

Immunization of rabbits: Rabbits were immunized with recombinant human (rh) PD-L1 Fc fusion (RnD Systems, USA, cat. no. 156-B7). Lymph nodes were extracted after the final boost and the cells were cryopreserved.

Confirmation of PD-L1 specificity: Confirmation of reactivity of rabbit sera to PD-L1 was carried out by binding ELISA. Briefly, PD-L1-Fc fusion (RnD Systems, USA, cat. no. 156-B7) or PD-L1-His (BioVision, USA, cat. no. 7429) were coated at a concentration of 2 mcg/mL in PBS for one hour at 37° C. onto Maxisorp 96-well microplates. After blocking with 5% non-fat dry milk and 1% BSA, increasing concentrations of rabbit serum were added, and bound IgGs detected by goat anti-rabbit IgG HRP (Southern Biotech, USA, cat. no. 4050-05). The ELISA was developed with TMB ELISA substrate solution (eBioscience, USA, cat. no. 00-4201-56). All rabbit sera bound to both Fc fused and His tagged PD-L1, showing that immunization successfully induced B cell response against PD-L1.

Flow cytometry sorting of rabbit B cells and culturing: PD-L1-specific memory B cells were sorted as single cells into 96-well microplates using FACSAria III (BD Biosciences). Single B cell clones were cultured in the presence of feeder cells and conditioned medium containing 10% fetal calf serum (FCS).

Over 900 single B cell clones were sorted, cultured and cell culture supernatants were analyzed by ELISA for the presence of anti-PD-L1-specific IgGs. Briefly, rhPD-L1 Fc fusion (RnD Systems, USA, cat. no. 156-B7) was coated at a concentration of 2 mcg/mL in PBS overnight at 4° C. onto Maxisorp 96-well microplates. After blocking with 5% non-fat dry milk, 1% BSA and 0.05% Tween-20, cell culture supernatants were added. PD-L1 specific IgGs were detected by anti-rabbit IgG-HRP (Southern Biotech, cat. no. 4050-05). The ELISA was developed with TMB ELISA substrate solution (eBioscience, USA, cat. no. 00-4201-56). PD-L1-specific IgG-producing B cell clones were identified and IgG antibodies were further analyzed for their ability to block the interaction of PD-L1 with PD-1. Briefly, PD-L1 expressing CHO cells (Promega, USA, cat. no. CS187103) were seeded into 96-well microplates. PD-L1-specific IgGs were added and plates incubated for 20 minutes at 37° C., 5% $CO_2$. PD-1 expressing effector Jurkat cells (Promega, USA, cat. no. CS187105) were added and the plates incubated for a further 6 hours at 37° C., 5% $CO_2$. TCR/CD3 activation was measured by luminescent detection with Bio-Glo Luciferase Assay System (Promega, G7941). 69 IgG-producing B cell clones were found to inhibit the interaction of PD-1 and PD-L1.

Sequencing of PD-L1-neutralizing IgGs: all rabbit B cell clones producing neutralizing anti-PD-L1 IgG antibodies were subjected to mRNA isolation using the RNeasy Mini Kit (Qiagen, Germany, cat. no. 74106). The mRNA was used as a template for reverse transcription according to the manufacture's protocol (OneStep RT-PCR kit, Qiagen, Germany, cat. no. 210212). Subsequently, PCR reactions using oligonucleotides to specifically amplify rabbit IgG heavy and light chain encoding sequences were carried out (Biometra Thermocycler T3). Heavy and light chain PCR fragments were independently sequenced (ABI, Sanger 3730x1; Microsynth AG, Balgach, Switzerland), and obtained nucleotide sequences were translated into amino acid sequences using EMBOSS Transeq (http://www.ebi.ac.uk/Tools/st/) and aligned using CLUSTALW2 (http://www.ebi.ac.uk/Tools/msa/clustalw2/).

Construction of anti-PD-L1 scFv genes and scFv protein expression: rabbit IgG CDR regions of the variable light and the variable heavy chains as defined above were identified and grafted onto human light and heavy chain acceptor frameworks. In some, point mutations were introduced. Bacterial expression vectors were generated encoding scFv proteins with the N-terminal variable light chain linked by the sequence SEQ ID No: 10 to the C-terminal variable heavy chain. ScFv proteins were expressed in *E. coli* BL21 (DE3); Novagen, USA, cat. no. 69450-3) as inclusion bodies, which were isolated, solubilized and the proteins were refolded. The refolded scFvs were purified by size exclusion chromatography and monomeric peak fractions corresponding to approximately 26 kDa were collected.

Humanized scFvs were analyzed for human PD-L1 Fc fusion binding by ELISA, as described above. By this procedure, out of 47 tested scFvs, 28 scFvs were identified as binders of human PD-L1. Humanized scFvs were further analyzed for binding to mouse PD-L1 by ELISA. Briefly, mouse PD-L1 Fc fusion (Sino Biological, China, cat. no. 50010-M03H or RnD Systems, USA, cat. no. 1019-B7-100) was coated at a concentration of 5 mcg/mL or 1 mcg/mL overnight at 4° C. onto Maxisorp 96-well microplates in PBS pH 7.2. After blocking with 1% BSA in PBS, pH7.2 or 5% non-fat dry milk with 1% BSA in PBS, pH7.2, increasing concentrations of scFv (0.0016, 0.008, 0.04, 0.2, 1.0 and 5.0 mcg/mL or 0.02, 0.06, 0.19, 0.56, 1.67 and 5.0 mcg/mL) were added to the wells. Successful coating of mouse PD-L1 Fc fusion was confirmed with a mouse PD-L1 specific antibody (Sino Biological, China, cat. no. 50010-M08H). Whereas the scFvs were detected by Protein L-HRP (Sigma-Aldrich, USA, cat. no. P3226), the full-length IgG control antibody was detected by goat anti-rabbit IgG conjugated to HRP (Southern Biotech, USA, cat. no. 4050-05). Development was with TMB ELISA substrate solution (eBioscience, USA, cat. no. 00-4201-56) and the absorbance was measured at 450 nm. ScFv1 did not cross-react with mouse PD-L1 up to a concentration of 5 mcg/mL. One tested scFv showed weak cross-reactivity to mouse PD-L1. Human PD-L1 binding scFvs were further characterized in their ability to neutralize the activity of human PD-L1, as shown in Example 2, their stability, as shown in Example 3, their affinity for human PD-L1, as shown in Example 4 and their specificity, as shown in Example 5. ScFv1 was further characterized by analysis of the binding to the natural form of human PD-L1, as shown in Example 6, by analysis of scFv1 secreted from cells, as shown in Example 7 and by determination of in vivo efficacy, as shown in Example 8. After conversion to IgG format, the antibody corresponding to scFv1 was further analysed by ability to inhibit the interaction between human PD-L1 and human PD-1 and by analysis of affinity to human PD-L1, as shown in Example 9.

Example 2—Neutralization of Human PD-L1

26 scFvs and one non-binding scFv (scFv2) were further tested for their PD-L1 neutralization capacity in a PD-1/PD-L1 blockade assay. In this assay, luciferase activity is promoted by the activity of T cells. The interaction of PD-L1 with PD-L1 creates an inhibitory signal and a reduction in luciferase activity, which is overcome by treatment of cells with an inhibitor of PD-L1. PD-L1 expressing CHO cells (Promega, CS187103) were seeded into 96-well microplates. Increasing concentrations of scFvs were added and plates incubated for 20 minutes at 37° C., 5% $CO_2$. PD-1 expressing effector Jurkat cells (Promega, CS187105) were added and the plates incubated for a further 6 hours at 37° C., 5% $CO_2$. TCR/CD3 activation was measured by luminescent detection with Bio-Glo Luciferase Assay System (Promega, G7941). Inhibition curves were plotted and the $IC_{50}$ values were calculated using GraphPad Prism® software, version 6.05. The results for scFv1 and scFv2 are shown in FIG. 1. ScFv1 efficiently blocked the immune checkpoint inhibitory signal with an $IC_{50}$ of 750 pM. The non-binding scFv2 did not show any effect on the immune checkpoint inhibitory signal. ScFv1 showed the highest potency of the 27 scFvs tested. The $IC_{50}$ of the lowest potency scFvs could not be determined using the concentration range of up to 10 mcg/mL.

Figure 2:
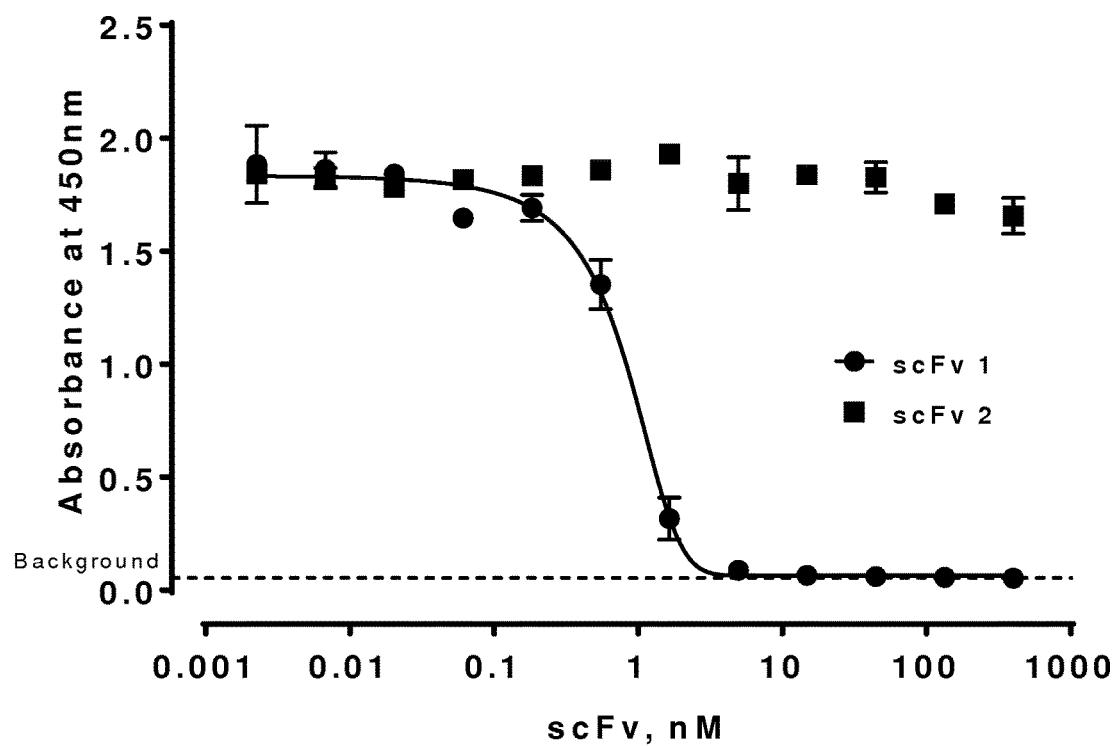
FIG. 2 shows that scFv1 blocks the interaction between rhPD-L1 and rhPD-1 in ELISA. Background level was determined in the absence of scFv and PD-1.

The ability of scFv1, the non-binding scFv2 and three other scFvs to inhibit the binding of PD-L1 to PD-1 was tested by competition ELISA. rhPD-L1 Fc fusion (RnD Systems, USA, cat. no. 156-B7) was coated at a concentration of 2 mcg/mL in PBS overnight at 4° C. onto Maxisorp 96-well microplates. Plates were blocked with 1% BSA and 0.05% Tween-20 in PBS, pH7.2. A serial dilution of scFvs was prepared, with eleven 1:3 dilutions starting at 1 mcg/mL, and added to plates. After one hour at room temperature, half of the scFv dilutions were removed and replaced with biotinylated PD-1 Fc fusion (BPS Bioscience, USA, cat. no. 71109) at a final concentration of 15 ng/mL. Bound PD-1 Fc fusion was detected with streptavidin-HRP (BD Pharmingen, USA, cat. no. 554060). Background level was determined in the absence of PD-1. The ELISA was developed with TMB ELISA substrate solution (eBioscience, USA, cat. no. 00-4201-56). In this assay, the ability of PD-L1 to interact with PD-1 generates an absorbance signal, which is effectively neutralized by scFv1 but not by the non-binding scFv2, as shown in FIG. 2. The three other scFvs also neutralized the interaction to an extent comparable to scFv1.

Figure 3:
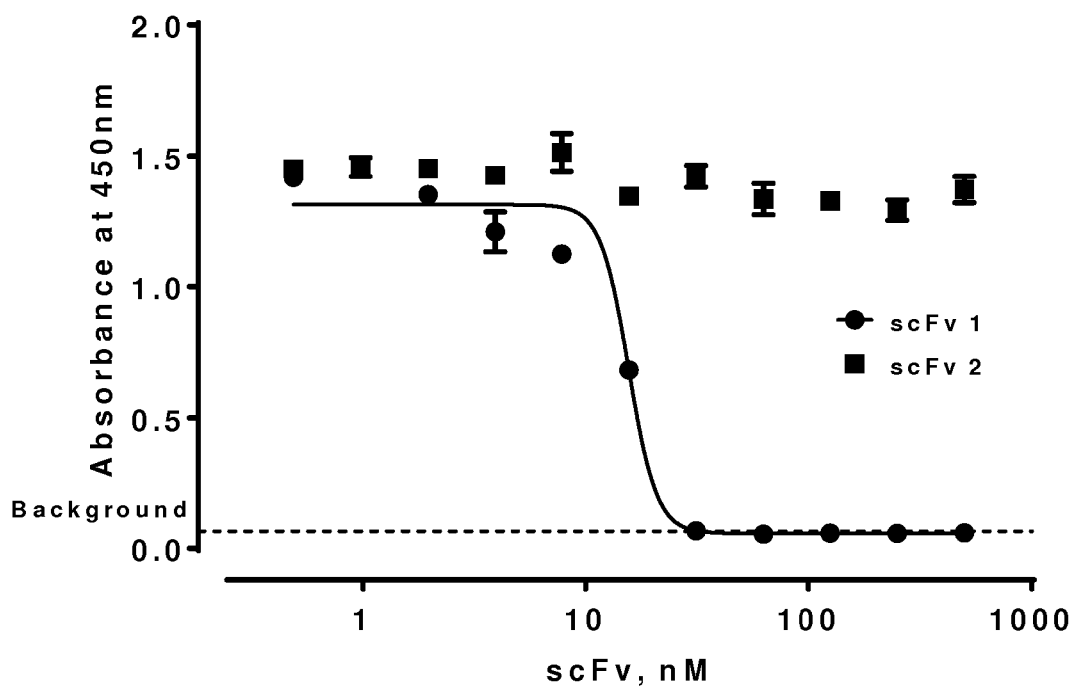
FIG. 3 shows that scFv1 blocks the interaction between rhPD-L1 and rhCD80 in ELISA. Background level was determined in the absence of PD-L1.

The ability of scFv1 and the non-binding scFv2 to inhibit the binding of PD-L1 to CD80 was tested by competition ELISA. rhCD80-His (RnD Systems, USA, cat. no. 9050-B1-100) was coated at a concentration of 2 mcg/mL in PBS overnight at 4° C. onto Maxisorp 96-well microplates. Plates were blocked with 1% BSA and 0.05% Tween-20 in PBS, pH7.4. A serial dilution of scFvs was prepared with a constant concentration of 50 nM rhPD-L1 Fc fusion (RnD Systems, USA, cat. no. 156-B7), with eleven 1:3 scFv dilutions starting at 1 mM. This mixture was incubated with the CD80 coated plates for 2 hours at room temperature. The background level corresponding to no binding of PD-L1 to CD80 was determined by including a dilution series of scFv1 in the absence of any PD-L1-Fc. Bound PD-L1 Fc fusion was detected with goat anti-human IgG Fc-HRP (Southern Biotech, USA, cat. no. 2048-05). The ELISA was developed with TMB ELISA substrate solution (eBioscience, USA, cat. no. 00-4201-56). In this assay, the ability of PD-L1 to interact with CD80 generates an absorbance signal, which is effectively neutralized to background level by scFv1 but not by the non-binding scFv2, as shown in FIG. 3.

Taken together, these results indicate that scFv1 blocks the interaction of PD-L1 with both PD-1 and CD80.

Example 3—Stability of scFvs

Two different processes can be observed that may affect the stability of scFvs. Firstly, the scFv could be prone to dimerization, often followed by oligomerization and further aggregation and precipitation. Secondly, scFv degradation, leading to smaller fragments, can occur over time. The stability of scFv1 and 4 other scFvs formulated in PBS pH 7.2 was investigated upon storage at different temperature conditions. The scFvs were stored at 10 mg/mL concentration at 4° C., 22° C., 37° C. and −20° C. in 1.5 mL polypropylene tubes. The samples were analyzed by SE-HPLC to determine the levels (%) of monomers, dimers and high molecular weight oligomers in relation to the total peak area: a TOSOH TSKgel G2000 SWXL column, phase diol, L×I.D. 30 cm×7.8 mm, 5 μm particle size (Sigma Aldrich, USA, cat no 08540) was used. 5 μL of scFvs at 10 mg/mL were loaded. As mobile phase PBS pH 7.2 was chosen.

ScFv1 was the most stable of the 5 scFvs tested. The SE-HPLC analysis of scFv1 showed no detectable low molecular weight degradation products in above described experimental conditions. Only a minor amount of dimerization of scFv1 or formation of high molecule weight molecules was observed upon storage for 2 weeks at 4° C., 22° C. and 37° C. ScFv1 formed up to 1.8% and 2.7% of dimers after 1 or 2 weeks of storage at 37° C., respectively (Table 1).

TABLE 1

| scFvs | Monomer content (%) | |
|---|---|---|
| | day 7 | day 14 |
| scFv1, 10 mg/ml, 4° C. | 99.23 | 99.15 |
| scFv1, 10 mg/ml, 22° C. | 99.07 | 98.91 |
| scFv1, 10 mg/ml, 37° C. | 98.17 | 97.29 |

The thermal stability of scFv1 was also assessed by differential scanning fluorimetry (DSF). scFv1 at 0.4 mg/mL formulated in PBS pH 7.2 was heated from 30° C. to 95° C. at a scan rate of 1° C./5 seconds in a real time PCR device (Corbett, Rotor-Gene) in the presence of 20× SYPRO® Orange (Sigma-Aldrich, USA, cat. no. S5692, 5000×) in PBS pH7.2. The fluorescence values were measured (excitation wavelength of 470 nm; emission wavelength of 555 nm) during the gradient run. The midpoint melting temperature (Tm) of scFv1 calculated using Rotor-Gene 6000 Series Software 1.7. was 81.5° C.

Proteinaceous biologics may become exposed to freeze/thaw stress during manufacturing, storing and shipping which may cause aggregation and degradation. In order to assess the stability of scFv1 during freeze/thaw cycles, it was formulated in PBS pH 7.2 at 10 mg/mL in 1.5 mL polypropylene tubes. The vials were submerged into liquid nitrogen for 1 min, then incubated in a water bath at room temperature for 5 min. 3, 5, 7 or 10 freeze/thaw cycles were performed. Samples were centrifuged for 10 minutes at 16,100×g and the pellet discarded. Supernatants were analyzed by SE-HPLC as mentioned above, and protein content determined by UV spectroscopy. Virtually 100% of scFv1 remained monomeric after 10 freeze/thaw cycles (Table 2) and no protein loss or precipitation was observed.

TABLE 2

| Freeze Thaw Cycles | Monomer Content (%) |
|---|---|
| 0 | 99.3 |
| 3 | 99.3 |
| 5 | 99.3 |
| 7 | 99.3 |
| 10 | 99.3 |

Figure 4:
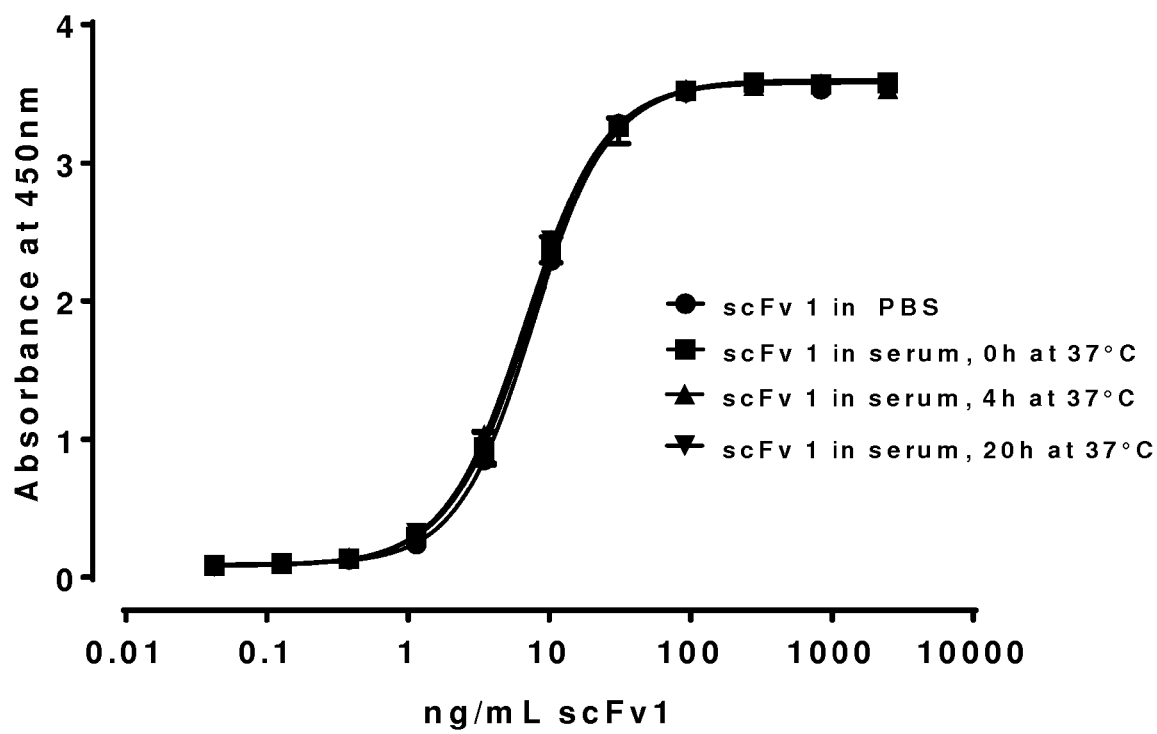
FIG. 4 shows that the ability of scFv1 to bind to rhPD-L1, measured by ELISA, is unaffected after storage at 37° C. in human serum.

The stability of scFv1 in human serum (Sigma-Aldrich, USA, cat no H4522) was assessed by ELISA after incubation at 10 mcg/mL at 37° C. for 0, 4 and 20 hours. The binding signal was compared with scFv1 in PBS, pH7.4, with no incubation. Briefly, rhPD-L1 Fc fusion (RnD Systems, USA, cat. no. 156-B7) was coated at a concentration of 1 mcg/mL in PBS overnight at 4° C. onto Maxisorp 96-well microplates. After blocking with PBS, pH7.4 with, 1% BSA and 0.05% Tween-20, a series of 1:3 dilutions of 2.5 mcg/ml to 42 ng/mL serum/scFv samples was added to the ELISA plates in duplicate. Bound scFv1 was detected with Protein L-HRP (Sigma-Aldrich, USA, cat. no. P3226). The ELISA was developed with TMB ELISA substrate solution (eBioscience, USA, cat. no. 00-4201-56). As shown in FIG. 4, there was no loss of binding activity of scFv1 after up to 20 hours of incubation with human serum at 37° C.

Example 4—Binding to Soluble PD-L1

Figure 5:
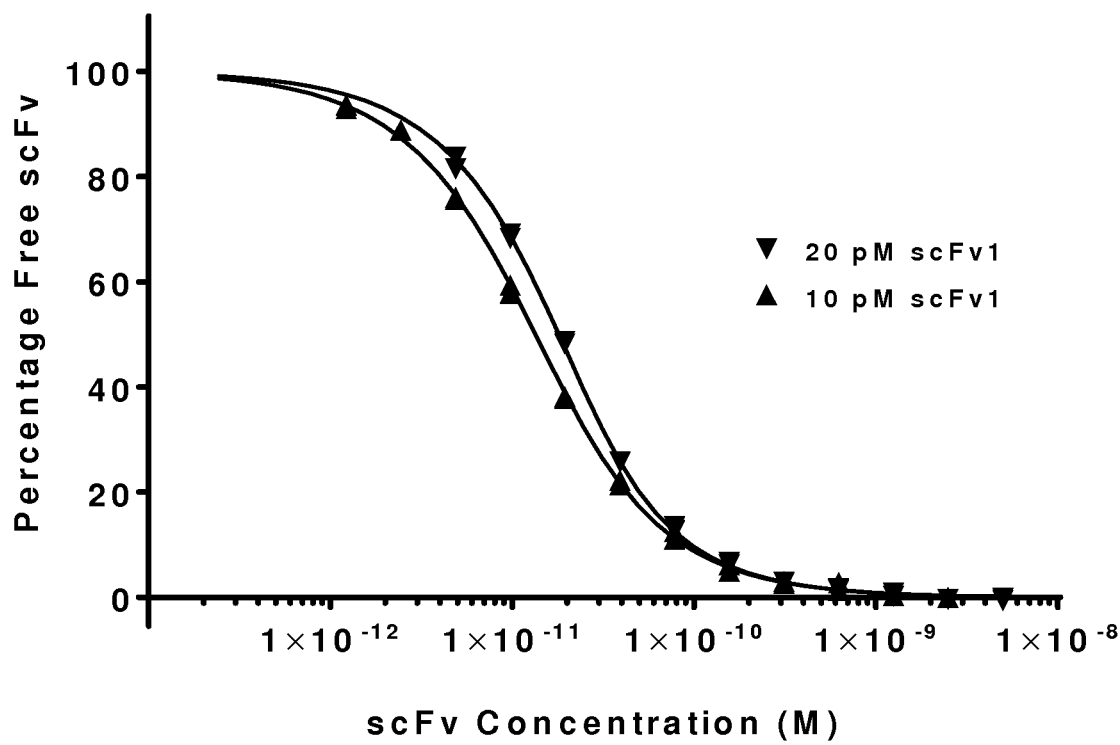
FIG. 5 shows that scFv1 binds to rhPD-L1 in a kinetic exclusion assay.

The affinity of scFv1 and three other scFvs to PD-L1-Fc fusion was determined by Kinetic Exclusion Assay (KinExA®) with a KinExA 3200 (Sapidyne Instruments, USA, cat. no. 5001) including autosampler (Sapidyne Instruments, USA, 5004). The KinExA® measures the equilibrium binding affinity and kinetics between unmodified molecules in solution. The measurement requires the immobilization of one interaction partner on a solid phase solely to act as a probe to determine the concentration of the corresponding binding partner in solution. Here, PD-L1 Fc fusion (RnD Systems, USA, cat. no. 156-B7) was immobilized onto Poly(methyl methacrylate) (PMMA) beads (440176, Sapidyne Instruments Inc.) at a concentration of 30 mcg/ml. PBS with 0.02% $NaN_3$, pH 7.4 was used as running buffer. Affinity of scFvs to PD-L1 Fc fusion was typically determined using a set of two curves, in which a 2-fold dilution series of PD-L1 Fc fusion was titrated against a constant amount of scFv. Duplicate measurements were prepared for each data point. For scFv1, in the first curve, 20 pM scFv1 was incubated with 11 different PD-L1 Fc fusion concentrations, starting with 5 nM PD-L1 Fc fusion. These mixtures were incubated for 5 hours. In a second curve, 10 pM scFv1 was incubated with 12 different PD-L1 Fc fusion concentrations, starting with 2.5 nM PD-L1 Fc fusion. These mixtures were incubated for 9 hours. To detect the amount of unbound scFv present in these mixtures, the samples were exposed at a flow rate of 0.25 ml/min to a solid phase containing immobilized PD-L1 Fc fusion. The captured scFv1 was then detected by injecting 0.5 mL of 250 ng/ml biotinylated Protein-L (M00097, GenScript), followed by 0.5 mL of 250 ng/mL streptavidin DyLight 650 conjugate (Jackson ImmunoResearch), each at a flow rate of 0.25 ml/min. All steps were carried out at room temperature. The fluorescence signal, which is directly proportional to the concentration of free scFv1 in the equilibrated samples, is converted to a voltage signal. This voltage signal is used to calculate the $K_D$ value and activity of the scFv using the "n-curve analysis" of the KinExA® Pro software version 4.1.9 or 4.2.10 (FIG. 5) using the option "titrant as analysis concentration reference". The $K_D$ value calculated for scFv1 was 8.8 pM. The $K_D$ value calculated for other scFvs ranged from 12 to 92 pM.

Example 5—Selectivity of scFvs

Figure 6:
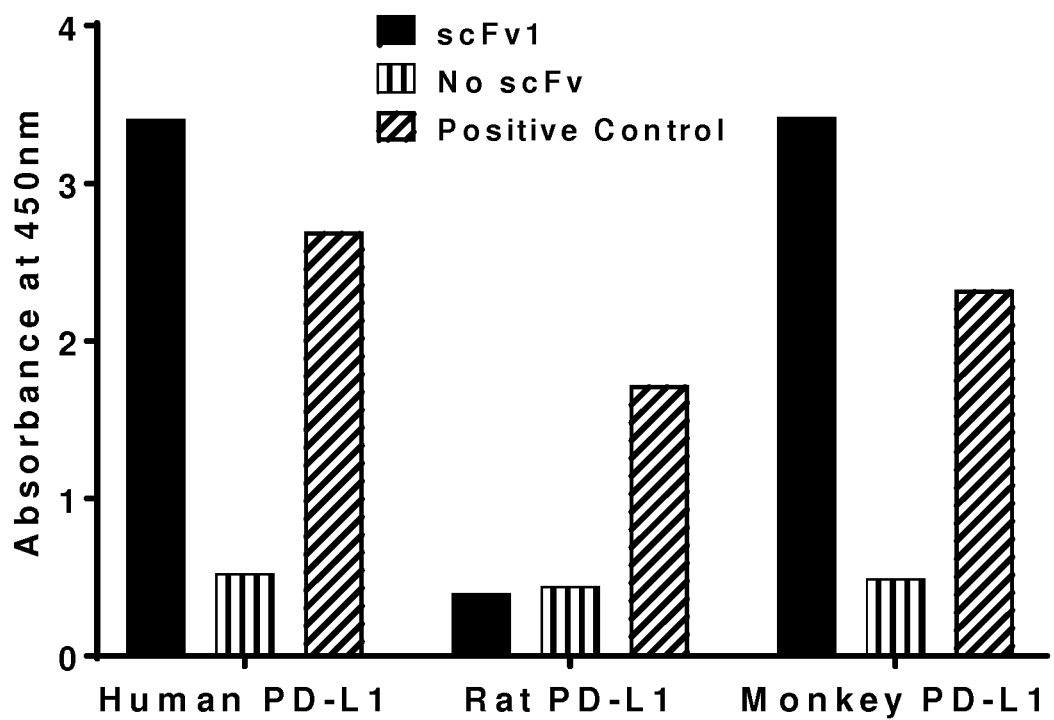
FIG. 6 shows that scFv1 binds to recombinant human and monkey PD-L1, but not to rat PD-L1, by binding ELISA. Background level is shown in the absence of scFv, and functionality of proteins is confirmed by use of a positive control antibody as defined in example 5.

Cross-reactivity of scFv1 and scFv3 to PD-L1 from other species was determined by ELISA. PD-L1 Fc fusions from human (RnD Systems, USA, cat. no. 156-B7), rat (Sino Biological, China, cat. no. 80450-R02H) or monkey (Sino Biological, China, cat. no. 90251-C02H) were coated overnight onto Maxisorp 96-well microplates at a concentration of 1 mcg/mL in PBS, pH 7.2 at 4° C. Plates were blocked with 1% BSA and 0.5% Tween-20 in PBS, pH7.2. A serial dilution of scFvs was prepared with concentrations of 1 mcg/mL, 333 ng/mL and 111 ng/mL and added to plates. As a negative control, PBS with no scFv was used, and as positive controls, 1 mcg/mL of mouse anti-human PD-L1 antibody (BioLegend, USA, cat. no. 329716) or biotinylated rhPD-1 Fc fusion (BPS Bioscience, USA, cat. no. 71109) was included. Bound scFvs were detected with Protein L-HRP (Sigma-Aldrich, USA, cat. no. P3226), bound mouse anti-human PD-L1 antibody was detected with goat anti-mouse IgG-HRP (Southern Biotech, USA, cat. no. 1033-01) and bound biotinylated rhPD-1 Fc fusion was detected with streptavidin-HRP (BD Pharmingen, USA, cat. no. 554060). Development was with TMB ELISA substrate solution (eBioscience, USA, cat. no. 00-4201-56). The results indicated that scFv1 and scFv3 specifically bound to human and monkey PD-L1, but not to rat PD-L1 (FIG. 6).

Cross-reactivity of scFv1 to recombinant human proteins sharing sequence similarity to PD-L1 was determined by ELISA. rhPD-L1 Fc fusion (RnD Systems, USA, cat. no. 156-B7), rhPD-L2 Fc fusion (RnD Systems, USA, cat. no. 1224-PL) or rhB7-H3 Fc fusion (RnD Systems, USA, cat. no. 1027-B3) were coated overnight onto Maxisorp 96-well microplates at a concentration of 1 mcg/mL in PBS, pH 7.2 at 4° C. Plates were blocked with 1% BSA and 0.5% Tween-20 in PBS, pH7.2. A serial dilution of scFvs was prepared with concentrations of 5, 1 and 0.2 mcg/mL and added to plates. As a negative control, the non-binding scFv2 was used, and as positive controls, 5, 1 and 0.2 mcg/mL of mouse anti-human B7-H3 antibody (RnD Systems, USA, cat. no. MAB1027) or 30 and 15 ng/mL of biotinylated rhPD-1 Fc fusion (BPS Bioscience, USA, cat. no. 71109) was included. Bound scFvs were detected with Protein L-HRP (Sigma-Aldrich, USA, cat. no. P3226), bound mouse anti-human B7-H3 antibody was detected with goat anti-mouse IgG-HRP (Southern Biotech, USA, cat. no. 1033-01) and bound biotinylated rhPD-1 Fc fusion was detected with streptavidin-HRP (BD Pharmingen, USA, cat. no. 554060).

Development was with TMB ELISA substrate solution (eBioscience, USA, cat. no. 00-4201-56). The results indicated that scFv1 specifically bound to human PD-L1, with no cross-reactivity to human PD-L2 or B7-H3.

Figure 7:
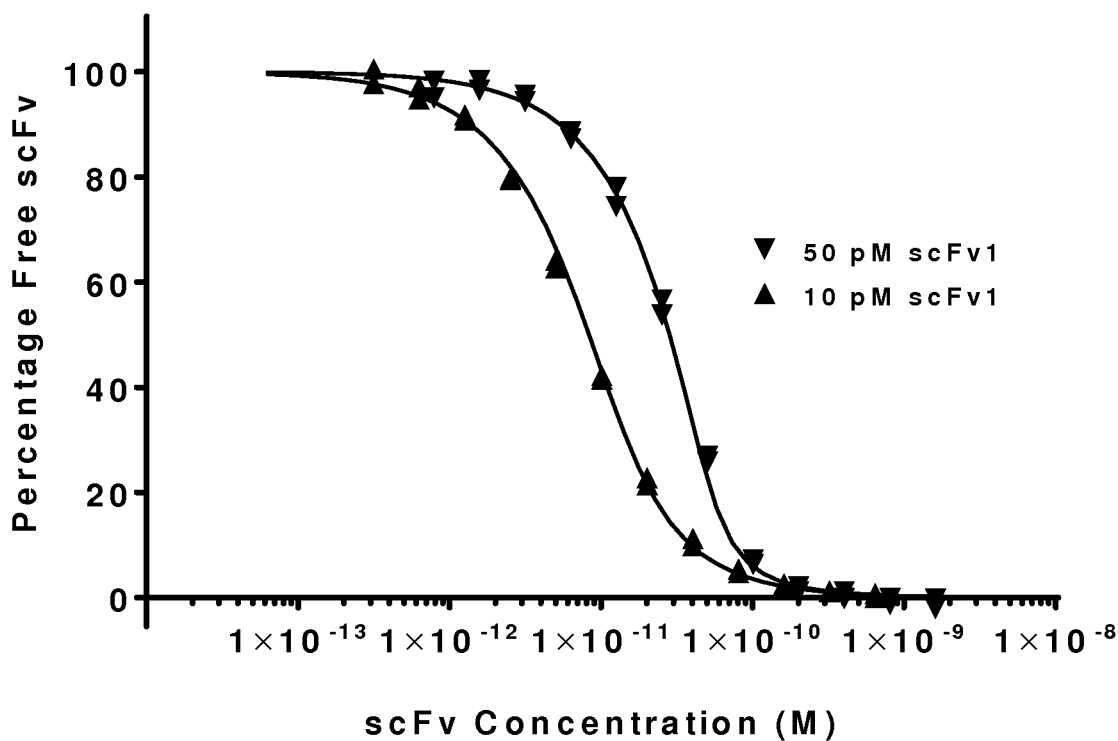
FIG. 7 shows that scFv1 binds to recombinant monkey PD-L1 in a kinetic exclusion assay.

Crossreactivity of scFv1 to monkey PD-L1 was further investigated using KinExA®. The method was as described in Example 4, except that PMMA beads were coated with 20 mcg/ml of monkey PD-L1 Fc fusion (Sino Biological, China, cat. no. 90251-C02H) and affinity was determined using a set of two curves, in which a 2-fold dilution series of monkey PD-L1 Fc fusion was titrated against a constant amount of scFv. In the first curve, 50 pM scFv1 was incubated with 12 different PD-L1 Fc fusion concentrations with duplicate measurements, starting with 2.5 nM PD-L1 Fc fusion. These mixtures were incubated for 6 hours. In a second curve, 10 pM scFv1 was incubated with 12 different PD-L1 Fc fusion concentrations, starting with 1 nM PD-L1 Fc fusion. These mixtures were incubated for 16 hours to detect the amount of unbound scFv present in these mixtures, the samples were exposed at a flow rate of 0.25 ml/min to a solid phase containing immobilized PD-L1 Fc fusion. All steps were carried out at room temperature. The $K_D$ value calculated for scFv1 using the "n-curve analysis" of the KinExA® Pro software version 4.2.10 using the option "titrant as analysis concentration reference" was 3.3 pM (FIG. 7). The results demonstrate that scFv1 binds to monkey PD-L1 with an affinity around 2.7 times tighter than binding to human PD-L1.

Example 6—Binding to the Natural Form of PD-L1

The ability of scFv1 and the non-binding control scFv, scFv2, to bind the natural form of PD-L1 expressed on the surface of tumor cells was determined by extracellular FACS analysis. ES-2 cells (ATCC, USA, cat. no. CRL-1978) were stained for 30 minutes on ice with 5 mcg/mL or 1 mcg/mL of scFvs or anti-human PD-L1 mouse IgG2 (BioLegend, USA, cat. no. 329716). Bound scFvs were detected by staining with biotinylated Protein L (Pierce, cat. no. PI-29997), followed by staining streptavidin-phycoerythrin (BD Pharmingen, USA, cat. no. 554061). After washing, propidium iodide was used to exclude dead cells and cells were analyzed on FACSAria III (BD Biosciences). The mean and median fluorescence intensities are shown in Table 3. The results demonstrate that scFv1 is able to specifically recognise the natural form of PD-L1 expressed on the surface of ES-2 cells.

TABLE 3

| Sample | Mean fluorescence intensity | Median fluorescence intensity |
| --- | --- | --- |
| Unstained ES-2 Cells | 62 | 50 |
| Positive Control IgG | 1172 | 948 |
| scFv1, 5 mcg/mL | 2739 | 2478 |
| scFv1, 1 mcg/mL | 2605 | 2338 |
| scFv2, 5 mcg/mL | 93 | 78 |

Figure 8:
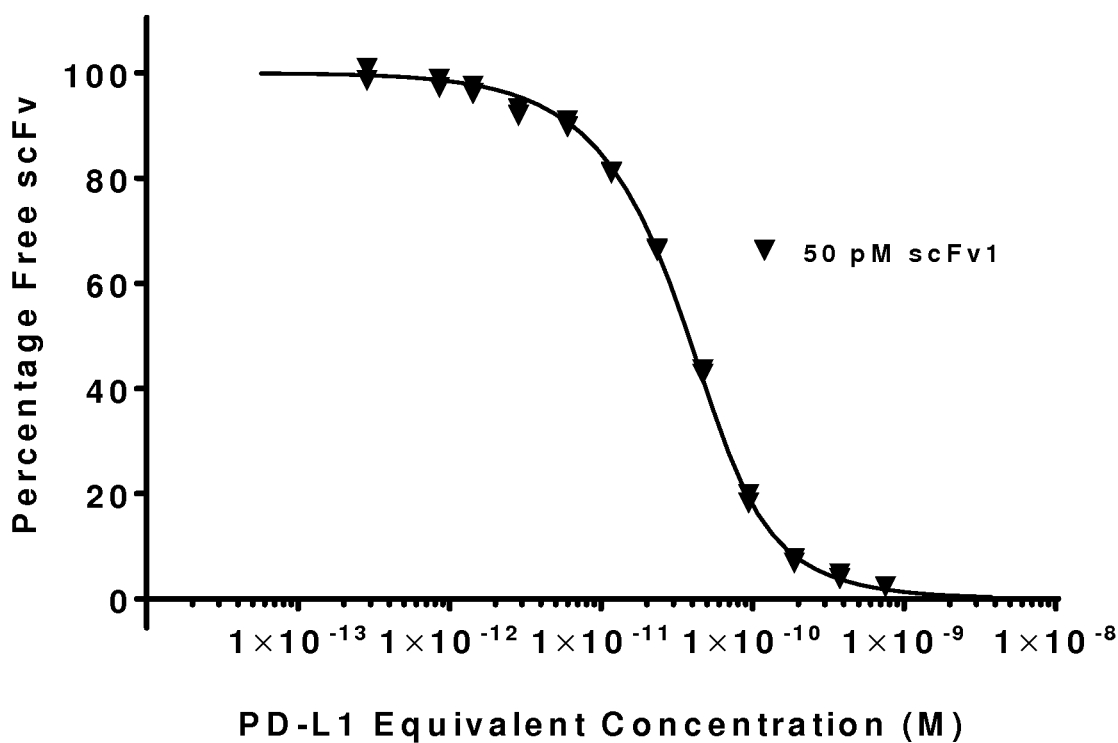
FIG. 8 shows that scFv1 binds to the human natural form of PD-L1 on the surface of cells in a kinetic exclusion assay.

The binding of scFv1 to cell surface PD-L1 was further investigated using KinExA®. The method was as described in Example 4, except that affinity was determined using twelve 2-fold serial dilutions of ES-2 cells (starting with 26.4 million per mL) which were titrated in duplicates against a constant amount of scFv1 (50 pM). These mixtures were incubated for 5 hours, centrifuged for 10 minutes at 3800×g, and supernatants were transferred to fresh tubes. To detect the amount of scFv, the samples were exposed at a flow rate of 0.25 ml/min to a solid phase containing immobilized PD-L1 Fc fusion. All steps were carried out at room temperature. Analysis using the KinExA® Pro software resulted in a calculated a $K_D$ value for scFv1 binding to cell surface PD-L1 of 12.8 pM (FIG. 8).

The results demonstrate that scFv1 binds the natural form of PD-L1 expressed on the surface of tumor cells.

Example 7—ScFv Secretion

In order to compare the properties of scFv1 produced in inclusion bodies by *E. coli* cells with the properties of scFv1 secreted from mammalian cells, scFv1 was produced in suspension-adapted CHO K1 cells (originally received from ATCC and adapted to serum-free growth in suspension culture) by Evitria (Zurich, Switzerland). The seed was grown in a chemically defined, animal-component free, serum-free medium. Cells were transfected with a custom-made, proprietary transfection reagent, and cells were grown after transfection in an animal-component free, serum-free medium. ScFv1 was purified by protein L affinity chromatography followed by size exclusion chromatography.

Figure 9:
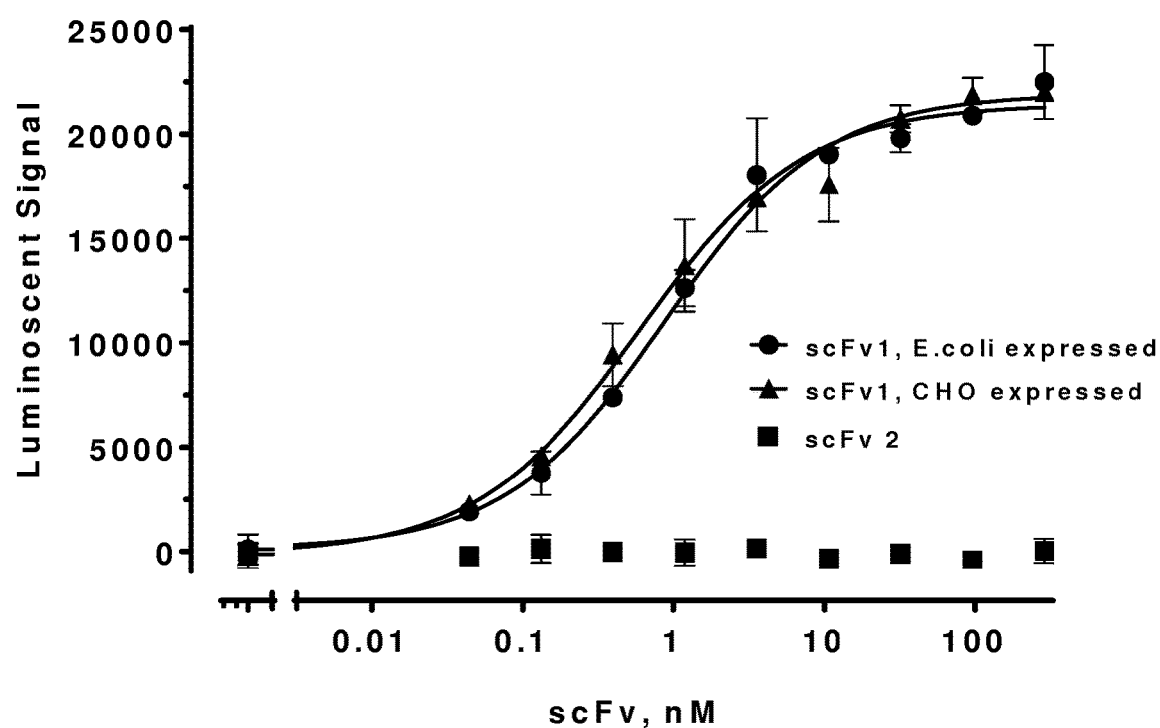
FIG. 9 shows that scFv1 produced from *E.Coli* inclusion bodies or secreted by CHO cells show similar inhibition of the interaction between PD-L1 and PD-1 in a cell based system.

The PD-L1 neutralization capacity of CHO cell and *E. coli* cell expressed scFv1 were compared in a PD-1/PD-L1 blockade assay. In this assay, luciferase activity is promoted by the activity of T cells. The interaction of PD-L1 with PD-1 creates an inhibitory signal and a reduction in luciferase activity, which is overcome by treatment of cells with an inhibitor of PD-L1. PD-L1 expressing CHO cells (Promega, CS187103) were seeded into 96-well microplates. Increasing concentrations of scFvs were added and plates incubated for 20 minutes at 37° C., 5% $CO_2$. PD-1 expressing effector Jurkat cells (Promega, CS187105) were added and the plates incubated for a further 6 hours at 37° C., 5% $CO_2$. TCR/CD3 activation was measured by luminescent detection with Bio-Glo Luciferase Assay System (Promega, G7941). Inhibition curves were plotted and the $IC_{50}$ values were calculated using GraphPad Prism® software, version 7.02. The results for CHO cell expressed scFv1, *E. coli* cell expressed scFv1 and scFv2 are shown in FIG. 9. CHO cell expressed scFv1 efficiently blocked the PD-L1 mediated inhibitory signal with an $IC_{50}$ of 602 pM. *E. coli* cell expressed scFv1 efficiently blocked the immune checkpoint inhibitory signal with an $IC_{50}$ of 874 pM. The non-binding scFv2 did not show any effect on the immune checkpoint inhibitory signal.

Example 8—In Vivo Activity

In vivo efficacy of scFv1 was examined using an HCC827 human lung cancer model in 5-6 week old female NOG mice (Vital River Laboratory Animal Technology Co., Beijing, China). Peripheral blood mononuclear cells (PBMC) were isolated from the blood of four healthy human donors by density gradient centrifugation using standard procedures. After centrifugation, cells were washed with PBS solution and resuspended in PBS. PBMC from each donor were transferred to mice by i.p. injection of $5\times10^6$ cells in 0.1 ml PBS three days before HCC827 tumour cell inoculation. Each mouse was then inoculated subcutaneously in the right flank region with $5\times10^6$ HCC827 tumor cells in 0.1 ml of PBS. The date of tumor cell inoculation was denoted as day 0. Mice were randomised on day 1 and treated twice daily with intraperitoneal (i.p.) injections of 15 mg/kg of scFv1 or the non-binding scFv2, or twice weekly with intravenous (i.v.) injections of 5 mg/kg of a positive control IgG antibody (an analogue of MPDL3280A). Tumor volume was measured at least twice weekly and expressed in mm3 using the formula $V=0.5\ a\times b^2$, where a and b are the length and width of the tumor, respectively. Tumour growth inhibition (TGI) is an indication of antitumor effectiveness, and expressed as TGI (%)=100×(1−(mean tumor volume of treated group)/(mean tumor volume of scFv2 group)). On day 14, the animals with PBMC from the two donors which showed greatest tumour growth inhibition were selected for continuation of the study. On day 21, all animals were sacrificed. Group size was n=3 per group per donor, for a total group size of n=6 with the two selected donors. The treatment over control ratio (T/C) was calculated as the ratio of the median tumor volumes of the scFv1 or positive control IgG treated group compared with the non-binding scFv2 control group, using the formula T/C (%)=(median tumor volume of treated group/median tumor volume of control group)×100.

Figure 10:
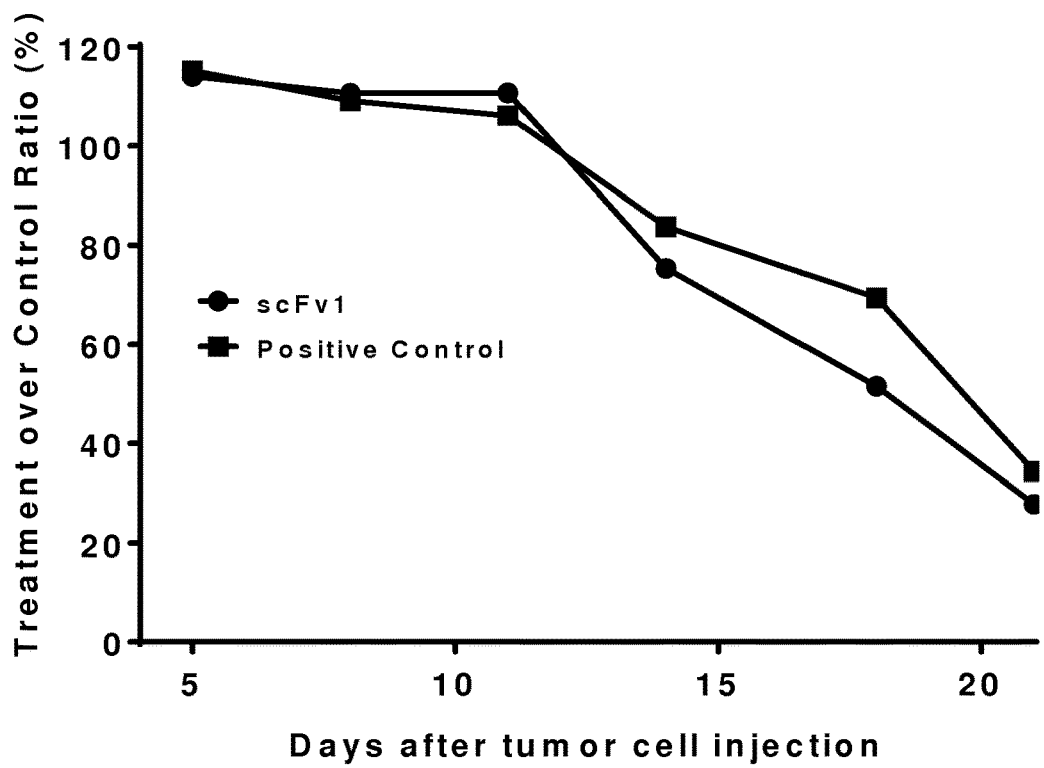
FIG. 10 shows that scFv1 promotes tumor shrinkage in a HCC827 human lung cancer model in nude mice which have been administered with human peripheral blood mononuclear cells (PBMCs). A: Treatment (scFv1 or positive control IgG) over control (non-binding scFv2) ratio as defined in example 8. B: Tumor growth inhibition (scFv1 or positive control IgG compared to non-binding scFv2) as defined in example 8.
Figure 10:
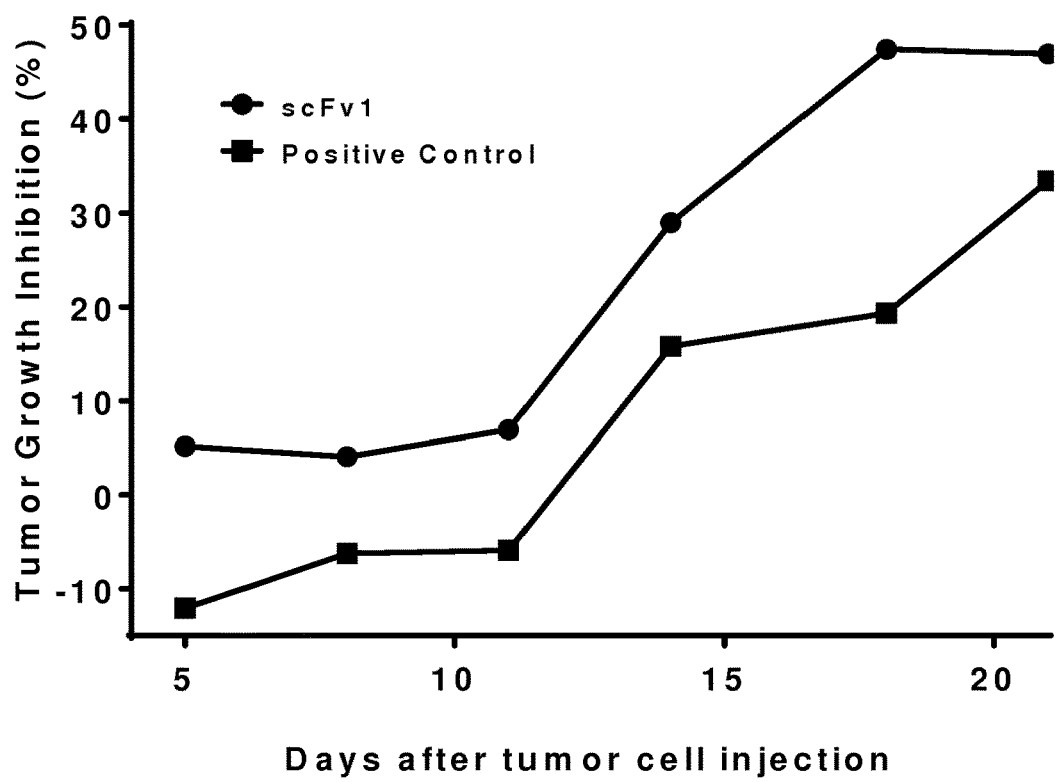

T/C and TGI for the two selected donors (n=6) is shown in FIG. 10. Efficacy of scFv1 and the positive control IgG antibody was evaluated on day 21 (Table 4). Three of the six scFv1 treated mice were tumor free, and TGI for scFv1 treated animals was 47%. The T/C ratio was 28%. The effective criteria for the T/C % ratio according to National Cancer Institute standards is ≤42%. Taken together, this data demonstrates in vivo efficacy of scFv1.

TABLE 4

| Treatment | TGI | T/C | Tumor free mice |
| --- | --- | --- | --- |
| scFv2, 15 mg/kg, i.p. twice daily | not applicable | not applicable | 0/6 |
| scFv1, 15 mg/kg, i.p. twice daily | 47% | 28% | 3/6 |
| Positive control IgG, 5 mg/kg, i.v. twice weekly | 33% | 34% | 2/6 |

Example 9—Characterization in IgG Format

ScFv1 was reformatted into IgG format (IgG_1), with heavy chain SEQ ID NO: 20 and light chain SEQ ID NO: 24. Also prepared were antibodies corresponding to the published sequence of YW243.55.570 as described in US2010/0203056 (IgG_2, with heavy chain SEQ ID NO: 21 and light chain SEQ ID NO: 25), 2.14H9OPT as described in WO2011/066389/A1 (IgG_3, with heavy chain SEQ ID NO: 22 and light chain SEQ ID NO: 26) and H2M8314N as described in WO2015/112805A1 (IgG_4, with heavy chain SEQ ID NO: 23 and light chain SEQ ID NO: 27). Synthesis was performed by Evitria (Zurich, Switzerland). Suspension-adapted CHO K1 cells originally received from ATCC and adapted to serum-free growth in suspension culture were used for production. IgG antibodies were purified by Protein A chromatography followed by size exclusion chromatography.

Figure 11:
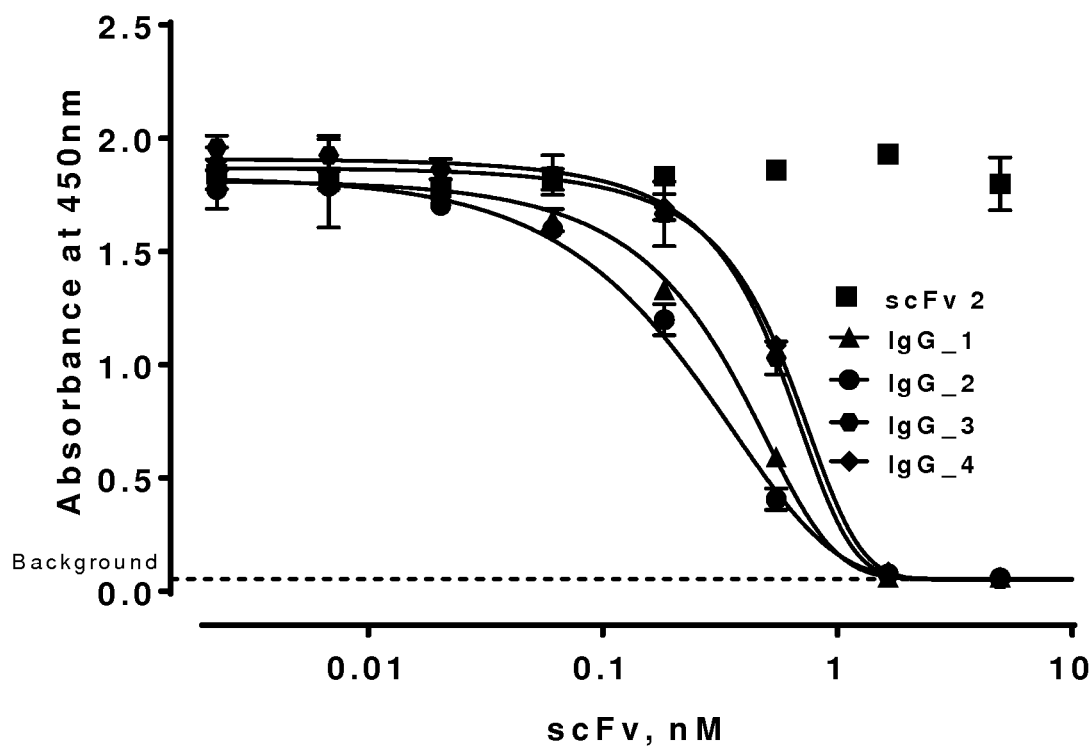
FIG. 11 shows that IgG_1 and IgG_2 are more effective than IgG_3 and IgG_4 in the inhibition of the interaction between rhPD-L1 and rhPD-1. Background level was determined in the absence of IgG and PD-1.

IgG antibodies were first characterized by examining the ability of the antibodies to inhibit the interaction of human PD-L1 with human PD-1. rhPD-L1 Fc fusion (RnD Systems, USA, cat. no. 156-B7) was coated at a concentration of 2 mcg/mL in PBS overnight at 4° C. onto Maxisorp 96-well microplates. Plates were blocked with 1% BSA and 0.05% Tween-20 in PBS, pH7.4. A serial dilution of IgGs was prepared, with eleven 1:3 dilutions starting at 1 mcg/mL, and added to plates. After 30 minutes at room temperature, half of the IgG dilutions were removed and replaced with biotinylated PD-1 Fc fusion (BPS Bioscience, USA, cat. no. 71109) at a final concentration of 15 ng/mL. Bound PD-1 Fc fusion was detected with streptavidin-HRP (BD Pharmingen, USA, cat. no. 554060). The ELISA was developed with TMB ELISA substrate solution (eBioscience, USA, cat. no. 00-4201-56). The non-binding scFv2 was included as a control. In this assay, the ability of PD-L1 to interact with PD-1 generates an absorbance signal, which is effectively neutralized by IgGs 1 to 4 but not by the non-binding scFv2, as shown in FIG. 11. The inhibition profiles of the antibodies tested fell into two groups, with the stronger potency IgG_1 and IgG_2 having IC50 values of 327 and 267 pM respectively. The weaker potency IgG_3 and IgG_4 had IC50 values of 560 and 606 pM respectively. The IgGs with stronger potency were taken forward for characterization of binding affinity.

Figure 12:
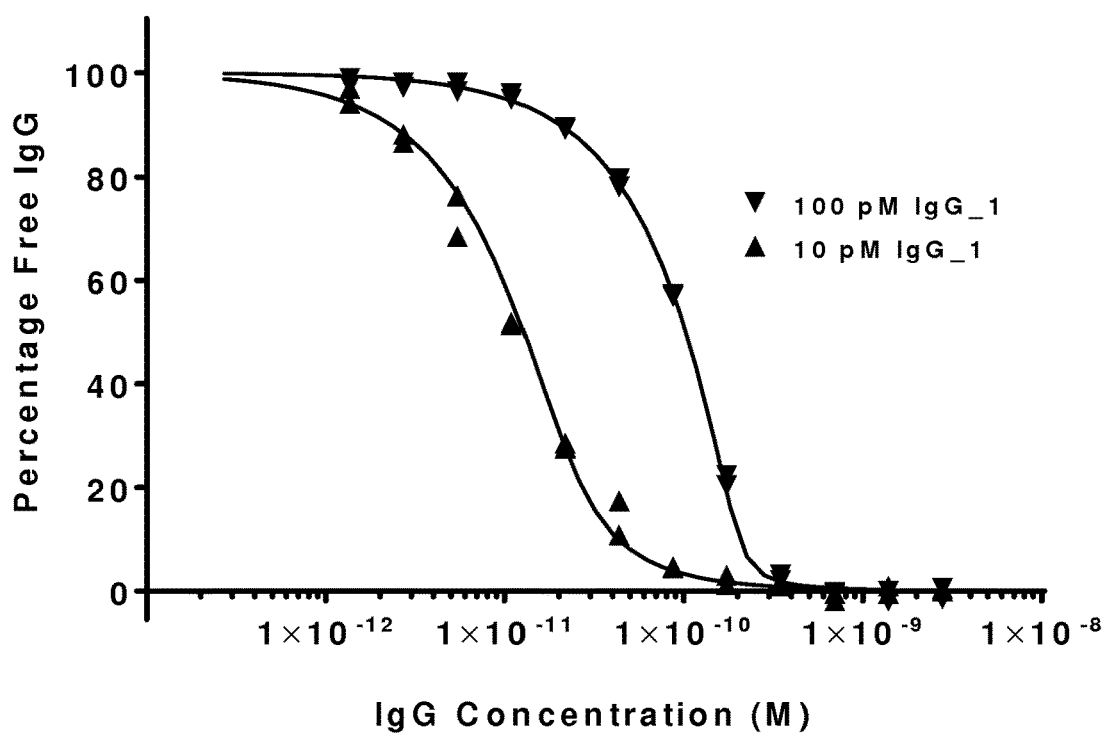
FIG. 12 shows that IgG_1 (A) has a tighter affinity than IgG_2 (B) in the interaction between IgG and PD-L1.
Figure 12:
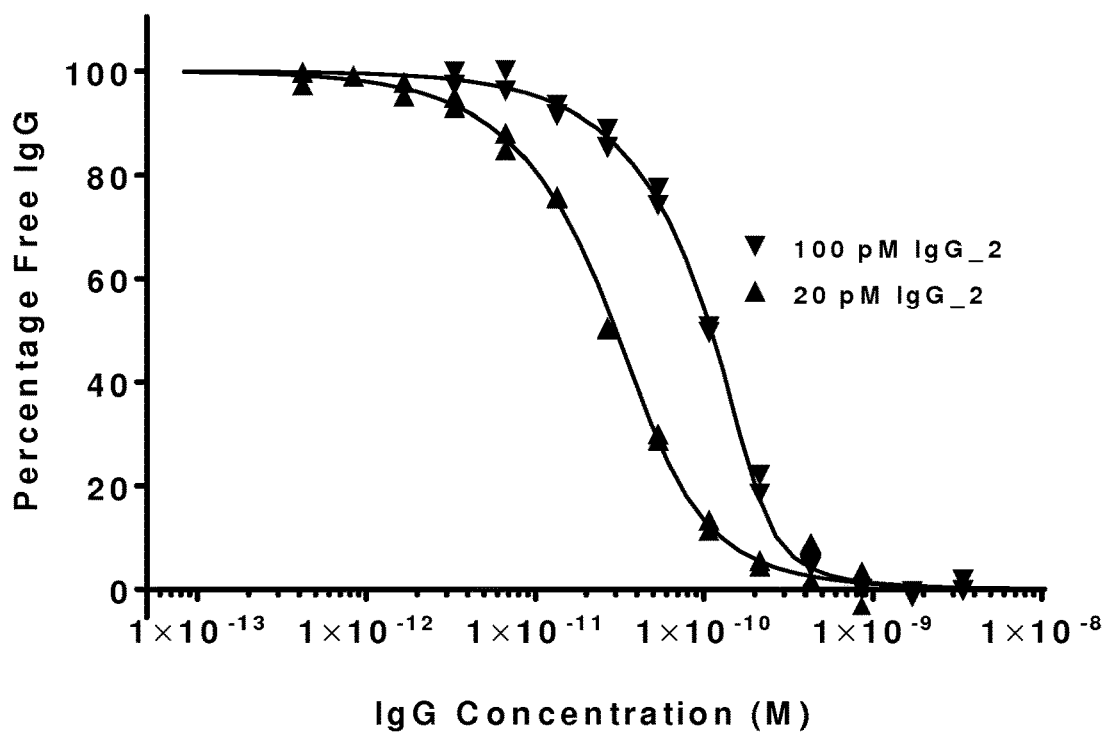

The binding of IgG_1 and IgG_2 to human PD-L1 was investigated using KinExA®. Although published data is available for the binding of IgG_2 to human PD-L1, this data is typically based on techniques which involve the immobilization of one interaction partner onto a solid surface. These approaches may not reflect the interaction conditions in solution, and also suffer from problems of sensitivity when examining very tight interactions. Therefore, a solution based method was chosen to compare the binding of the antibodies. PD-L1-His without an Fc tag was chosen as interaction partner to avoid measurement of avidity. The method was as described in Example 4, except that affinity was determined using a set of two curves, in which a 2-fold dilution series of human PD-L1-His (BioVision, USA, cat. no. 7429) was titrated against a constant amount of scFv. For both IgGs, in the first curve, 100 pM of IgG was incubated with 12 different PD-L1 Fc fusion concentrations with duplicate measurements, starting with 5 nM PD-L1-His. These mixtures were incubated for 5 hours. 500 microlitres of each sample was injected onto the human PD-L1 Fc fusion coated beads. For IgG_1, in a second curve, 10 pM of IgG was incubated with 12 different PD-L1-His concentrations, starting with 5 nM PD-L1 His. These mixtures were incubated for 10 hours. 5 ml of each sample was injected onto the PD-L1 Fc fusion coated PMMA beads. For IgG_2, in a second curve, 20 pM of IgG was incubated with 12 different PD-L1-His concentrations, starting with 1.25 nM PD-L1 His. These mixtures were incubated for 10 hours. 5 ml of each sample was injected onto the PD-L1 Fc fusion coated PMMA beads. The $K_D$ values calculated for IgGs are reported in Table 5 and n-curve analysis shown in FIG. 12.

The results demonstrate that IgG_1 (i.e., the scFv1 converted into IgG format) binds PD-L1 with an affinity around three times tighter than the affinity of scFv1 to PD-L1. IgG_2 has weaker affinity to PD-L1 when compared to IgG_1.

TABLE 5

| Antibody | $K_D$ (pM) |
| --- | --- |
| IgG_1 | 2.77 |
| IgG_2 | 10.06 |

While presently preferred embodiments of the invention are shown and described, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

The invention claimed is:

1. A binding member having a binding specificity to PD-L1, comprising
   (i) the variable heavy chain CDR-H1, CDR-H2 and CDR-H3 sequences as set forth in SEQ ID NOs: 6, 7 and 8; and
   (ii) the variable light chain CDR-L1, CDR-L2 and CDR-L3 sequences as set forth in SEQ ID NOs: 3, 4 and 5,
wherein said binding member is chemically modified.

2. The binding member of claim 1, being humanized.

3. The binding member of claim 1, further comprising a linker sequence set forth in SEQ ID NO: 10.

4. The binding member of claim 1, wherein said binding member is multivalent.

5. The binding member of claim 1, wherein said binding member comprises an Fc domain.

6. The binding member of claim 5, wherein said binding member comprises a constant region selected from the group consisting of a human IgG1, IgG2, IgG3, and IgG4 isotype.

7. The binding member of claim 5, wherein said binding member comprises a constant region selected from the group consisting of a murine IgG1, IgG2A, IgG2B, and IgG3 isotype.

8. The binding member of claim 5, wherein said Fc domain is modified and does not induce a cytotoxic immune response.

9. The binding member of claim 1, wherein said chemical modification is PEGylation, HESylation, or conjugation to a second moiety.

10. A method of producing a binding member of having a binding specificity to PD-L1, the method comprising:
   (i) cultivating a host cell comprising a nucleic acid molecule comprising a sequence encoding a binding member having a binding specificity to PD-L1 and comprising the variable heavy chain CDR-H1, CDR-H2 and CDR-H3 sequences as set forth in SEQ ID NOs: 6, 7 and 8, and the variable light chain CDR-L1, CDR-L2 and CDR-L3 sequences as set forth in SEQ ID NOs: 3, 4 and 5, thereby allowing the binding member to be expressed; and
   (ii) recovering the binding member.

11. A method of producing a binding member having a binding specificity to PD-L1, the method comprising:
   (a) contacting a cell-free expression system with a nucleic acid product template, the nucleic acid product template encoding a binding member having a binding specificity to PD-L1 and comprising the variable heavy chain CDR-H1, CDR-H2 and CDR-H3 sequences as set forth in SEQ ID NOs: 6, 7 and 8, and the variable light chain CDR-L1, CDR-L2 and CDR-L3 sequences as set forth in SEQ ID NOs: 3, 4 and 5 according to claim 1;
   (b) allowing transcription and translation of the nucleic acid product template to occur, thereby allowing a reaction mixture to be formed;
   (c) recovering the binding member from the reaction mixture.

12. The method of producing a binding member of claim 10, further comprising purifying said binding member.

13. A method of detecting the presence of PD-L1 in a biological sample, the method comprising:
   (a) contacting the biological sample with a binding member having a binding specificity to PD-L1 and comprising the variable heavy chain CDR-H1, CDR-H2 and CDR-H3 sequences as set forth in SEQ ID NOs: 6, 7 and 8, and the variable light chain CDR-L1, CDR-L2 and CDR-L3 sequences as set forth in SEQ ID NOs: 3, 4 and 5 under conditions permissive for specific binding of the binding member to PD-L1, and
   (b) detecting whether a complex between the binding member and PD-L1 is formed.

14. The method of claim 13, wherein said method is an in vitro method or an in vivo method.

15. The method of claim 13, wherein said biological sample is of human origin.

16. The method of claim 13, wherein said biological sample is at least one of a blood sample, a urine sample, a cerebrospinal fluid sample, a biopsy sample, or a lymph sample.

17. The method of claim 13, wherein said method is a method for selecting subjects eligible for therapy with a binding member having a binding specificity to PD-L1.

18. The binding member of claim 4, wherein said multivalent binding member is multispecific, bispecific, a diabody, a single chain diabody, a DART, a BiTE, or a tandem scFv.

* * * * *